US009506087B2

(12) United States Patent
Vroom et al.

(10) Patent No.: US 9,506,087 B2
(45) Date of Patent: Nov. 29, 2016

(54) GLUCOSE AND XYLOSE CO-UTILIZATION IN *E. COLI*

(71) Applicant: Codexis, Inc., Redwood City, CA (US)

(72) Inventors: Jonathan A. Vroom, South San Francisco, CA (US); Fernando Valle, Burlingame, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 14/419,706

(22) PCT Filed: Aug. 6, 2013

(86) PCT No.: PCT/US2013/053741
§ 371 (c)(1),
(2) Date: Feb. 5, 2015

(87) PCT Pub. No.: WO2014/025747
PCT Pub. Date: Feb. 13, 2014

(65) Prior Publication Data
US 2015/0225745 A1  Aug. 13, 2015

Related U.S. Application Data

(60) Provisional application No. 61/680,676, filed on Aug. 7, 2012.

(51) Int. Cl.
*C12P 7/04* (2006.01)
*C12N 9/10* (2006.01)
*C12N 9/12* (2006.01)
*C12N 15/70* (2006.01)
*C12P 7/10* (2006.01)
*C07K 14/195* (2006.01)
*C12N 15/52* (2006.01)

(52) U.S. Cl.
CPC .............. *C12P 7/04* (2013.01); *C07K 14/195* (2013.01); *C12N 15/52* (2013.01); *C12N 15/70* (2013.01); *C12P 7/10* (2013.01); *Y02E 50/16* (2013.01)

(58) Field of Classification Search
CPC .............. C12P 7/04; C12P 7/16; C12P 7/42; C12N 9/88
USPC .......... 435/134, 157, 158, 136, 160, 252.33, 435/197
See application file for complete search history.

(56) References Cited

U.S. PATENT DOCUMENTS

| 5,602,030 | A | 2/1997 | Ingrahm et al. |
| 5,770,435 | A | 6/1998 | Donnelly et al. |
| 6,117,679 | A | 9/2000 | Stemmer |
| 6,159,738 | A | 12/2000 | Donnelly et al. |
| 6,376,246 | B1 | 4/2002 | Crameri et al. |
| 6,586,182 | B1 | 7/2003 | Patten et al. |
| 7,790,432 | B2 | 9/2010 | Chatterjee et al. |
| 8,389,214 | B2 | 3/2013 | Cervin et al. |
| 8,476,041 | B2 | 7/2013 | Cervin et al. |
| 8,871,489 | B2 * | 10/2014 | Grabar ................ C07K 14/245 435/145 |
| 2003/0017559 | A1 | 1/2003 | Donnelly et al. |
| 2008/0104724 | A1 | 5/2008 | Sticklen et al. |
| 2008/0220990 | A1 | 9/2008 | Fox |
| 2009/0142843 | A1 | 6/2009 | Cervin et al. |
| 2009/0312196 | A1 | 12/2009 | Colbeck et al. |
| 2012/0202259 | A1 * | 8/2012 | Grabar ................ C07K 14/245 435/136 |

FOREIGN PATENT DOCUMENTS

WO  2011/016706 A2  2/2011

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Altschul, S., et al., "Basic local alignment search tool," J. Mol. Biol., 215: 403-410 (1990).
Altschul, S.F., et al., "Gapped BLAST and PSI-BLAST: a new generation of protein database search programs," Nucleic Acids Res., 25(17):3389-3402 (1997).
Baez-Viveros, J.L., et al., "Metabolic transcription analysis of engineered *Escherichia coli* strains that overproduce L-phenylalanine," Microb. Cell Fact., 6(30):1-20 [2007].
Chatterjee, R., et al., "Mutation of the ptsG Gene Results in Increased Production of Succinate in Fermentation of Glucose by *Escherichia coli*," Appl. Environ. Microbiol., 67:148-154 [2001].
Datsenko, K.A., et al., "One-step inactivation of chromosomal genes in *Escherichia coli* K-12 using PCR products," PNAS, 97(12): 6640-6645 [2000].
Datta, S., et al., "A set of recombineering plasmids for gram-negative bacteria," Gene, 379: 109-115 (2006).
De Ruse, H., et al., "The ptsH, ptsI, and crr genes of the *Escherichia coli* phosphoenolpyruvate-dependent phosphotransferase system: a complex operon with several modes of transcription," J. Bacteriol., 170(9):3827-37 [1988].
Gosset, G., "Improvement of *Escherichia coli* production strains by modification of the phosphoenolpyruvate:sugar phosphotransferase system," Microb. Cell Fact., 4(14):1-11 [2005].
Groff, D., et al., "Supplementation of Intracellular XylR Leads to Coutilization of Hemicellulose Sugars," Appl. Environ. Microbio., 78(7):2221-2229 [2012].
Henderson, P.J.F., "Proton-linked sugar transport systems in bacteria," J. Bioener. Biomembr., 22(4):525-69 [1990].
Henderson, P.J.F., et al., "Homologous Sugar Transport Proteins in *Escherichia coli* and Their Relatives in Both Prokaryotes and Eukaryotes," Philos. Trans. R. Soc. Lond. B Biol. Sci., 326(1236):391-410 [1990].
Henikoff, S.,et al., "Amino acid substitution matrices from protein blocks," Proc. Natl. Acad. Sci., 89:10915-10919 (1992).

(Continued)

*Primary Examiner* — Robert Mondesi
*Assistant Examiner* — Md. Younus Meah
(74) *Attorney, Agent, or Firm* — Codexis, Inc.

(57) ABSTRACT

The present invention provides host cells having improved sugar utilization or co-utilization, methods of producing host cells having improved sugar utilization or co-utilization, and methods of using host cells having improved sugar utilization or co-utilization. The present invention provides *E. coli* strains that co-utilize glucose and xylose in the presence of glucose and xylose, wherein the cell produces the product.

7 Claims, 7 Drawing Sheets

(56) References Cited

OTHER PUBLICATIONS

Hernandez-Montalvo, V., et al., "Expression of galP and glk in a *Escherichia coli* PTS Mutant Restores Glucose Transport and Increases Glycolytic Flux to Fermentation Products," Biotech Bioeng., 83:687-94 [2003].

Jojima, T., et al., "Sugar transporters in efficient utilization of mixed sugar substrates: current knowledge and outlook," Appl. Microbiol. Biotechnol., DOI 10.1007/s00253-009-2292-1 [2009].

Kim, J.H., et al., "Simultaneous consumption of pentose and hexose sugars: an optimal microbial phenotype for efficient fermentation of lignocellulosic biomass," Appl. Microbiol. Biotechnol., 88:1077-1085 [2010].

Kouvelis, V.N., et al., "Genome Sequence of the Ethanol-Producing *Zymomonas mobilis* subsp. pomaceae Lectotype Strain ATCC 29192," J. Bacterial., 193(18):5049-5050 [2011].

Lathe, R., et al., "Plasmid and bacteriophage vectors for excision of intact inserts," Gene, 57:193-201 [1987].

Lu, J., et al., "Combinatorial modulation of galP and glk geneexpression for improved alternative glucose utilization," Appl. Microbiol. Biotechnol., DOI 10.1007/s00253-011-3752-y [2011].

Needleman, S., et al., "A general method applicable to the search for similarities in the amino acid sequence of two proteins," J. Mol. Biol. 48:443-453 (1970).

Nevoigt, E., et al., "Engineering of Promoter Replacement Cassettes for Fine-Tuning of Gene Expression in *Saccharomyces cerevisiae*," Appl. Environ. Microbiol., 72:5266-5273 (2006).

Nichols., N.N., et al., "Use of catabolite repression mutants for fermentation of sugar mixtures to ethanol," Appl. Microbiol. Biotechnol., 56:120-125 [2001].

Pearson, W.R., "Improved tools for biological sequence comparison," Proc. Nat'l. Acad. Sci. USA, 85:2444-2448 (1988).

Postma, P.W., et al., "Phosphoenolpyruvate:Carbohydrate Phosphotransferase Systems of Bacteria," Microbiol. Rev., 57(3):543-94 [1993].

Ren, C et al., "An evolved xylose transporter from Zymomonas mobilis enhances sugar transport in *Escherichia coli*," Microb. Cell Fact, 8:66, pp. 1-9 [2009].

Ricciardelli, C., et al., "Development and characterization of primary cultures of smooth muscle cells from the fibromuscular stroma of the guinea pig prostate," In Vitro Cell Dev. Biol., 25:1016-1024 [1989].

Rud, I.,et al., "A synthetic promoter library for constitutive gene expression in Lactobacillus plantarum ," Microbiol., 152:1011-1019 [2006].

Smith, T.F., et al., "Comparison of Biosequences," Adv. Appl. Math., 2:482-489 [1981].

Snoep, J.L., et al., "Reconstruction of glucose uptake and phosphorylation in a glucose-negative mutant of *Escherichia coli* by using Zymomonas mobilis genes encoding the glucose facilitator protein and glucokinase," J. Bacteriol., 176(7):2133-35 [1994].

Tchieu, J.H., et al., "The Complete Phosphotransferase System in *Escherichia coli*," J. Mol. Microbiol. Biotechnol., 3 (3):329-46 [2001].

Weisser, P., et al., "Functional Expression of the Glucose Transporter of Zymomonas mobilis Leads to Restoration of Glucose and Fructose Uptake in *Escherichia coli* Mutants and Provides Evidence for Its Facilitator Action," J. Bacteriol., 177(11):3351-54 [1995].

* cited by examiner

```
MSSESSSQGLVTRLALIAAIGGLLFGYDSAVIAAIGIPVDINFIGPRHLSATAAASLSGMVVVAVLAGCVVGSLISGWMGI    Pom
MSSESSSQGLVTRLALIAAIGGLLFGYDSAVIAAIGTPVDIHFIAPRHLSATAAASLSGMVVVAVLVGCVTGSLLSGWIGI    glf
**********************************    ****  **  **********************  ***  *** ***  **
         1         2         3         4         5         6         7         8
12345678901234567890123456789012345678901234567890123456789012345678901234567890

RFGRRGGLLISAVCFIISGFGAAT-TGLTGDIGSALPIFCFFRFLGGFGIGIVSTLTPTYIAEIAPPDKRGQMVSGQQMA    Pom
RFGRRGGLLMSSICFVAAGFGAALTEKLFGTGGSALQIFCFFRFLAGLGIGVVSTLTPTYIAEIAPPDKRGQMVSGQQMA    glf
**********  **   **   *****   *  *     ****    * *** ************************
         9        10        11        12        13        14        15         1
12345678901234567890123456789012345678901234567890123456789012345678901234567890

IVTGALTGYIFTWLLAHFGSVDWINANGWRWSPASEGIIAVVFLLLLLTAPDTPHWLVMKGRHSEASKIIARLEPQVDPS    Pom
IVTGALTGYIFTWLLAHFGSIDWVNASGWCWSPASEGLIGIAFLLLLLTAPDTPHWLVMKGRHSEASKIIARLEPQADPN    glf
********************  ** ** ** **  *****  **  ** ******************************
        17        18        19        20        21        22        23         2
12345678901234567890123456789012345678901234567890123456789012345678901234567890

LTIQKIRAGFDKALQKSNSGLFAFGATVIFAGVSVAMFQQLVGINAVLYYAPQMFLNLGFGADTALLQTISIGVVNFVFT    Pom
LTIQKIRAGFDKAMDKSSAGLFAFGITVVFAGVSVAAFQQLVGINAVLYYAPQMFQNLGFGADTALLQTISIGVVNFIFT    glf
*************  ** ******* ** *******  ******************* ****************** **
        25        26        27        28        29        30        31         3
12345678901234567890123456789012345678901234567890123456789012345678901234567890

MIASRIVDREGRKPLLIWGGIAMAVMMFSLGMMFTYHIGGVLPLAAILLYIVGFAMSWGPVCWVLSEMFPNAIKGSAMP    Pom
MIASRVVDREGRKPLLIWGALGMAAMMAVLGCCFWFKVGGVLPASVLLYIAVFGMSWGPVCWVLSEMFPSSIKGAAMP    glf
*****  ************   **  ** **  **    ****   ***** * ******************  *** ***
        33        34        35        36        37        38        39         4
12345678901234567890123456789012345678901234567890123456789012345678901234

IAVTAQWIANILVNFLFKIADGDPGLNRTFNHGFSYLVFAGLSILGALIVARFVPETKGRSLEEIEEMWRS--    Pom
IAVTGQWLANILVNFLFKVADGSPALNQTFNHGFSYLVFAALSILGGLIVARFVPETKGRSLDEIEEMWRSQK    glf
****  ** *********  **** ** ***********   **** ***************  ********
        41        42        43        44        45        46        47
12345678901234567890123456789012345678901234567890123456789012345678901234 sequence identity = 84.68%
```

FIG. 1

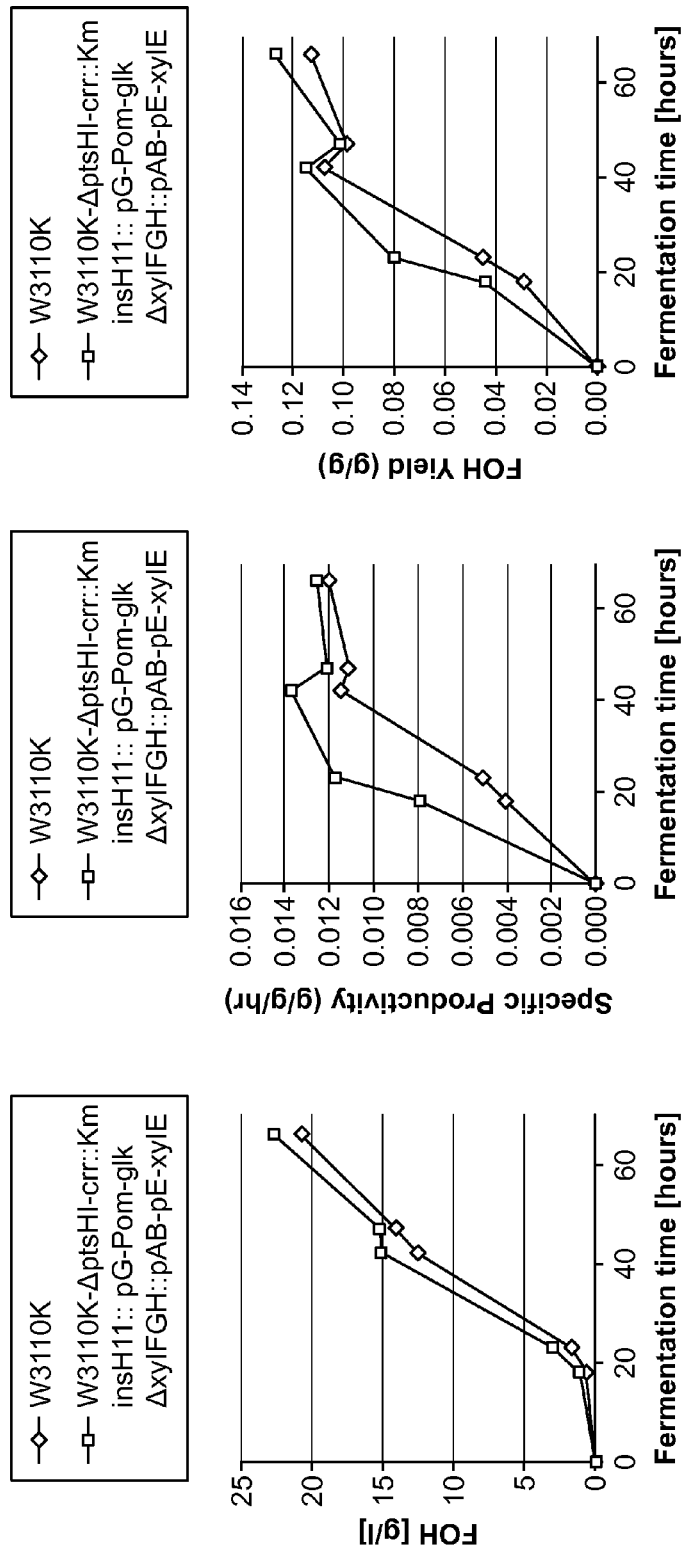

FOH (g/L)

| Growth Time [hours] | W3110K | W3110K-ΔptsHI-crr::Km insH11:: pG-Pom-glk ΔxylFGH::pAB-pE-xylE |
|---|---|---|
| 0 | 0.0 | 0.0 |
| 18 | 0.6 | 1.1 |
| 23 | 1.7 | 3.0 |
| 42 | 12.5 | 15.1 |
| 47 | 14.1 | 15.2 |
| 66 | 20.7 | 22.7 |

Specific Productivity (g/g/hr)

| Growth Time [hours] | W3110K | W3110K-ΔptsHI-crr::Km insH11:: pG-Pom-glk ΔxylFGH::pAB-pE-xylE |
|---|---|---|
| 0 | 0.0000 | 0.0000 |
| 18 | 0.0040 | 0.0079 |
| 23 | 0.0051 | 0.0117 |
| 42 | 0.0115 | 0.0137 |
| 47 | 0.0111 | 0.0121 |
| 66 | 0.0120 | 0.0126 |

FOH Yield (g/g)

| Growth Time [hours] | W3110K | W3110K-ΔptsHI-crr::Km insH11:: pG-Pom-glk ΔxylFGH::pAB-pE-xylE |
|---|---|---|
| 0 | 0.000 | 0.000 |
| 18 | 0.029 | 0.045 |
| 23 | 0.045 | 0.081 |
| 42 | 0.108 | 0.115 |
| 47 | 0.099 | 0.101 |
| 66 | 0.113 | 0.127 |

GLUCOSE AND XYLOSE CO-UTILIZATION IN E. COLI

The present application is a national stage application filed under 35 USC §371 and claims priority to international application to PCT International Application No. PCT/US2013/053741, filed Aug. 6, 2013, which claims priority to previously filed U.S. Provisional Application. No. 61/680,676 filed Aug. 7, 2012, both of which are hereby incorporated in their entireties for all purposes.

REFERENCE TO A SEQUENCE LISTING, A TABLE OR A COMPUTER PROGRAM LISTING APPENDIX SUBMITTED AS AN ASCII TEXT FILE

The Sequence Listing written in file CX5-123WO1_ST25.TXT, created on Jul. 24, 2013, 39,936 bytes, machine format IBM-PC, MS Windows operating system, is hereby incorporated by reference.

FIELD OF THE INVENTION

The present invention provides host cells having improved sugar utilization or co-utilization, methods of producing host cells having improved sugar utilization or co-utilization, and methods of using host cells having improved sugar utilization or co-utilization.

BACKGROUND OF THE INVENTION

In E. coli, the transport of glucose across the cell membrane is facilitated by the phosphoenolpyruvate (PEP)-dependent phosphotransferase transfer system (PTS). The PTS system is part of a complex regulatory system that allows E. coli to control numerous metabolic pathways in response to the presence of glucose. However, in the presence of glucose, a cell with an intact PTS system preferentially utilizes glucose and represses other sugar utilization pathways, a phenomenon known as "catabolic repression." Thus, a host cell having an intact PTS system that is fed a mixture of glucose plus xylose preferentially consumes glucose before xylose. Deleting all or part of the PTS system can decouple glucose transport from the effects of catabolic repression, but also impairs the ability of the cell to utilize glucose and various other sugars. Thus, there remains a need in the art for methods of restoring high levels of glucose transport in PTS negative strains. Additionally, there remains a need for methods of increasing co-utilization of multiple types of sugar in microbial host cells.

BRIEF DESCRIPTION OF THE DRAWINGS

FIG. 1 provides an amino acid alignment between the putative sugar transport gene product from *Zymomonas mobilis* subsp. *pomaceae* (ATCC 29192) (SEQ ID NO:2) and the *Z. mobilis* subsp. *mobilis* (ZM4) glf gene product (SEQ ID NO:3). These sequences are approximately 85% (84.68%) identical.

FIG. 3 provides graphs showing fatty alcohol titer, specific productivity, and fatty alcohol yield. Panel A provides the fatty alcohol (FOH) titer, Panel B provides the specific productivity (grams of FOH per gram of cellulosic sugar per hour), and Panel C provides the FOH yield (grams of FOH per gram of cellulosic sugar) for *E. coli* strains W3110K and W3110K-ΔptsHI-crr::Km—insH11::pG-Pom-glk—ΔxylFGH::pAB-pE-xylE transformed with a plasmid expressing a fatty alcohol forming reductase (FAR), derived from *Marinobacter algicola* strain DG893, when grown in ten liter fermentors using cellulosic hydrolysate as the primary carbon and energy source. Panel D provides a Table showing data plotted in Panels A-C. In this Table, the fatty alcohol (FOH) titer (left panel) corresponds to (a); specific productivity (grams of FOH per gram of cellulosic sugar per hour) (middle panel) corresponds to (b); and FOH yield (grams of FOH per gram of cellulosic sugar) (right panel) corresponds to (c).

SUMMARY OF THE INVENTION

Figure 2B:
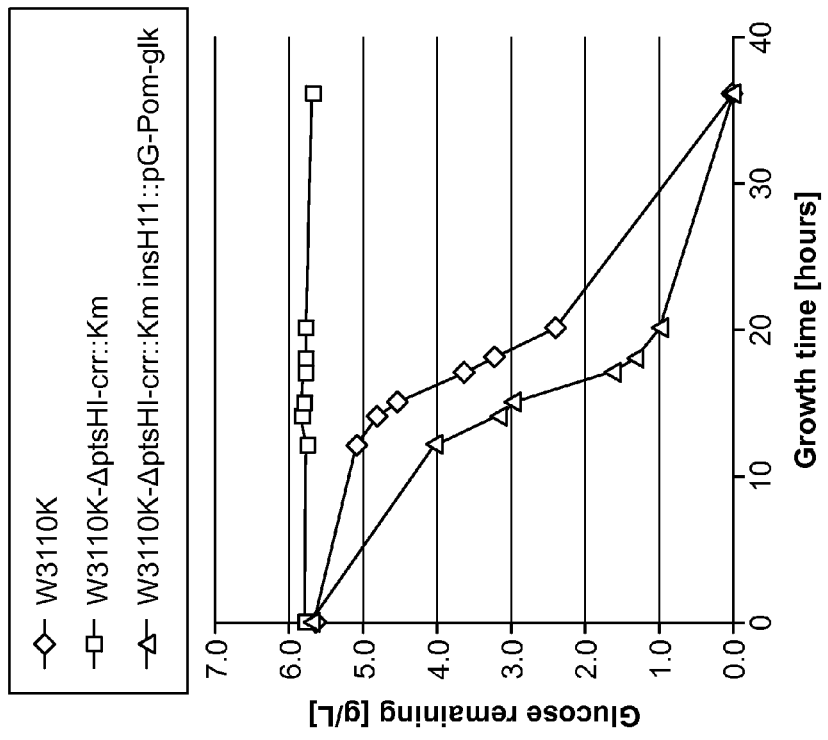
FIG. 2 provides a graphs showing cell growth curves (a) and glucose consumption (b) for *E. coli* cell lines W3110K, W3110K-ΔptsHI-crr::Km, and W3110K-ΔptsHI-crr::Km—insH11::pG-Pom-glk. Panel A shows the cell growth curves and Panel B shows the glucose consumption for cells grown in shake flask in M9 minimal media supplemented with 0.5% glucose. Strain W3110K-ΔptsHI-crr::Km did not utilize glucose well. Expression of the putative glf gene from *Zymomonas mobilis* subsp. *pomaceae* (ATCC 29192) and the native glk gene in W3110K-ΔptsHI-crr restored glucose utilization and growth on glucose to levels in excess of the W3110K wild-type cells.

The present invention provides host cells having improved sugar utilization or co-utilization, methods of producing host cells having improved sugar utilization or co-utilization, and methods of using host cells having improved sugar utilization or co-utilization.

The present invention provides *E. coli* strains that co-utilize glucose and xylose. The present invention also provides methods of producing a product comprising culturing an *E. coli* cell that co-utilizes glucose and xylose in the presence of glucose and xylose, wherein the cell produces the product. In some embodiments, the cell is recombinantly engineered to produce the product. In some additional embodiments, the product is an alcohol, an organic acid, a hydrocarbon, an amino acid, a fatty-acid derivative, a diol, or a drug or drug precursor. In some further embodiments, the glucose and xylose are the products of saccharification. In some embodiments, the glucose and xylose are the products of saccharification of a cellulosic material or a cellulosic biomass. In still some further embodiments, the culturing is in a medium comprising about 2 parts glucose to about 1 part xylose. In still some further embodiments, the culturing is in a medium comprising 2 parts glucose to 1 part xylose.

The present invention also provides methods of producing a modified host cell having a phosphoenolpyruvate-dependent phosphotransferase transfer system negative (PTS⁻) phenotype and capable of co-utilization of glucose and xylose, the method comprising: (a) modifying the host cell to express (i) a first gene encoding a polypeptide having glucose transport activity, wherein the first gene is operably linked to a first heterologous promoter, and wherein the polypeptide having glucose transport activity has at least about 85% sequence identity to the amino acid sequence of SEQ ID NO:2; and (ii) a second gene encoding a polypeptide having xylose transport activity, wherein the second gene is operably linked to a second heterologous promoter; wherein the host cell in (a) is PTS−, or wherein the host cell is made PTS⁻ before, during or after the modifications of (i) and (ii) are made; and (b) culturing the modified host cell under suitable culture conditions. In some embodiments, the present invention also provides methods of producing a modified host cell having a phosphoenolpyruvate-dependent phosphotransferase transfer system negative (PTS⁻) phenotype and capable of co-utilization of glucose and xylose, the method comprising: (a) modifying the host cell to express (i) a first gene encoding a polypeptide having glucose transport activity, wherein the first gene is operably linked to a first heterologous promoter, and wherein the polypeptide having glucose transport activity has at least 85% sequence identity to the amino acid sequence of SEQ ID NO:2; and (ii) a second gene encoding a polypeptide having xylose transport activity, wherein the second gene is operably linked to a second heterologous promoter; wherein the host cell in (a) is PTS⁻, or wherein the host cell is made PTS⁻ before, during or after the modifications of (i) and (ii) are made; and (b) culturing the modified host cell under suitable culture conditions. In some embodiments, the first gene encoding a polypeptide having glucose transport activity has at least 85% sequence identity to the polynucleotide sequence of SEQ ID NO:1. In some additional embodiments, the first gene comprises the polynucleotide sequence set forth in SEQ ID NO:1. In some embodiments, the host cell is a bacterial host cell. In some additional embodiments, the host cell is E. coli. In some further embodiments, the first gene encodes a polypeptide having the amino acid sequence of SEQ ID NO:2. In some embodiments, the second gene encodes a xylose symporter protein. In some further embodiments, the xylose symporter protein is xylE. In some additional embodiments, the methods further comprise modifying the host cell to express a third gene encoding a glucokinase protein, wherein the third gene is operably linked to a third heterologous promoter. In some embodiments, one or more of the first promoter, second promoter, or third promoter is a constitutive promoter. In some further embodiments, one or more of the first promoter, second promoter, or third promoter is a constitutive promoter library. In yet some additional embodiments, one or more of the first gene, second gene, or third gene is integrated into the genome of the modified host cell. In some further embodiments, the PTS⁻ phenotype is caused by deletion or inactivation of all or substantially all of one or more of genes selected from ptsH, ptsI, and crr. In some additional embodiments, the host cell is further modified to delete or substantially inactivate an endogenous gene encoding a xylose ABC transporter. In some embodiments, the modified host cell exhibits at least a 10% increase in glucose and xylose co-utilization as compared to an unmodified host cell. The present invention also provides modified host cells produced by any of the embodiments described herein.

The present invention also provides methods for producing an end-product from a biomass substrate comprising one or more sugars, the method comprising: providing a host cell, wherein the host cell has a phosphoenolpyruvate-dependent phosphotransferase transfer system negative (PTS⁻) phenotype and wherein the host cell has been modified to express: (i) a first gene encoding a polypeptide having glucose transport activity, wherein the first gene is operably linked to a first heterologous promoter, and wherein the polypeptide having glucose transport activity has at least 85% sequence identity to the amino acid sequence of SEQ ID NO:2; and (ii) a second gene encoding a polypeptide having xylose transport activity, wherein the second gene is operably linked to a second heterologous promoter; contacting the modified host cell with the biomass substrate; and culturing the modified host cell under suitable culture conditions; thereby producing the end-product. In some embodiments, the biomass substrate comprises glucose and xylose. In some further embodiments, the host cell is a bacterial host cell. In some additional embodiments, the host cell is E. coli. In some embodiments, the first gene encodes a polypeptide having the amino acid sequence of SEQ ID NO:2. In some additional embodiments, the first gene comprises a polynucleotide sequence that has at least 85% identity to SEQ ID NO:1. In some additional embodiments, the first gene comprises the polynucleotide sequence set forth in SEQ ID NO:1. In some embodiments, the second gene encodes a xylose symporter protein. In some additional embodiments, the xylose symporter protein is xylE. In some further embodiments, the methods further comprise modifying the host cell to express a third gene encoding a glucokinase protein, wherein the third gene is operably linked to a third heterologous promoter. In some embodiments, one or more of the first promoter, second promoter, or third promoter is a constitutive promoter. In some embodiments, one or more of the first promoter, second promoter, or third promoter is a constitutive promoter library. In some additional embodiments, one or more of the first gene, second gene, or third gene is integrated into the genome of the host cell. In some embodiments, the host cell is further modified to delete or substantially inactivate an endogenous gene encoding a xylose ABC transporter. In some additional embodiments, the PTS phenotype is caused by deletion or inactivation of all or substantially all of one or more of genes selected from ptsH, ptsI, and crr. In some further embodiments, the end-product comprises at least one alcohol, while in some additional embodiments, the end-product comprises at least one hydrocarbon. In some further embodiments, the end-product is an alcohol, while in some additional embodiments, the end-product is a hydrocarbon.

The present invention also provides host cells having a phosphoenolpyruvate-dependent phosphotransferase transfer system negative (PTS⁻) phenotype and capable of co-utilization of glucose and xylose, wherein the host cell comprises: (a) a first gene encoding a polypeptide having glucose transport activity, wherein the first gene is operably linked to a first heterologous promoter, and wherein the polypeptide having glucose transport activity has at least 85% sequence identity to the amino acid sequence of SEQ ID NO:2; and (b) a second encoding a polypeptide having xylose transport activity, wherein the second gene is operably linked to a second heterologous promoter. In some further embodiments, the host cell is a bacterial host cell. In some additional embodiments, the host cell is *E. coli*. In some embodiments, the first gene encodes a polypeptide having the amino acid sequence of SEQ ID NO:2. In some additional embodiments, the first gene comprises a polynucleotide sequence that has at least 85% identity to SEQ ID NO:1. In some additional embodiments, the first gene comprises the polynucleotide sequence set forth in SEQ ID NO:1. In some embodiments, the second gene encodes a xylose symporter protein. In some additional embodiments, the xylose symporter protein is xylE. In some embodiments, the host cell further comprises a third gene encoding a glucokinase protein, wherein the third gene is operably linked to a third heterologous promoter. In some embodiments, one or more of the first promoter, second promoter, or third promoter is a constitutive promoter. In some embodiments, one or more of the first promoter, second promoter, or third promoter is a constitutive promoter library. In some additional embodiments, one or more of the first gene, second gene, or third gene is integrated into the genome of the host cell. In some embodiments, the host cell is further modified to delete or substantially inactivate an endogenous gene encoding a xylose ABC transporter. In some additional embodiments, the PTS⁻ phenotype is caused by deletion or inactivation of all or substantially all of one or more of genes selected from ptsH, ptsI, and crr. In some further embodiments, the modified host cell exhibits at least a 10% increase in glucose and xylose co-utilization as compared to an unmodified host cell.

DESCRIPTION OF THE INVENTION

The present invention provides host cells having improved sugar utilization or co-utilization, methods of producing host cells having improved sugar utilization or co-utilization, and methods of using host cells having improved sugar utilization or co-utilization.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in analytical chemistry, cell culture, molecular genetics, organic chemistry, and nucleic acid chemistry and hybridization described below are those well-known and commonly employed in the art. It is noted that as used herein, "a," "an," and "the" include plural references unless the context clearly dictates otherwise. The term "comprising" and its cognates are used in their inclusive sense; that is, equivalent to the term "including" and its corresponding cognates.

The techniques and procedures are generally performed according to conventional methods in the art and various general references (See, e.g., Sambrook et al., *Molecular Cloning: A Laboratory Manual,* 3rd ed. [2001]; Ausubel, ed., *Current Protocols in Molecular Biology* [1990-2008]; and C. A. Reddy et al., *Methods for General and Molecular Microbiology,* 3rd Edition, ASM Press, [2007]). Standard techniques, or modifications thereof, are used for nucleic acid and polypeptide synthesis and for chemical syntheses and chemical analyses. Generally, enzymatic reactions and purification steps are performed according to the manufacturer's specifications.

There are some reports regarding the use of alternative glucose transporters in PTS negative strains in order to restore high levels of glucose transport (See e.g., U.S. Pat. Nos. 8,476,041 and 8,389,214). In particular, native galactose permease (galP) and native glucokinase (glk) have been co-expressed (See e.g., Hernandez-Montalvo et al., Biotechnol Bioeng. 83:687-94 [2003]), and glucose facilitator (glf) and glk from *Zymomonas mobilis* subsp. *mobilis* (ZM4) have been co-expressed (See e.g., Snoep et al., J. Bacteriol., 176:2133-35 [1994]). However, there remains a need in the art for methods of restoring high levels of glucose transport in PTS negative strains. Additionally, there remains a need for methods of increasing co-utilization of multiple types of sugar in microbial host cells. The present invention meets these heretofore unmet needs, as described herein.

The term "phosphoenolpyruvate-dependent phosphotransferase transfer system" or "PTS" refers to the phosphoenolpyruvate (PEP)-dependent carbohydrate uptake system that transports and phosphorylates carbohydrates (e.g., sugars) at the expense of PEP. The PTS includes two proteins, enzyme I and HPr, that are common to all carbohydrates, and a number of carbohydrate-specific enzymes, the enzymes II. The PTS system known (See e.g., Tchieu et al., J. Mol. Microbiol. Biotechnol., 3:329-46 [2001]; and Postma et al., Microbiol. Rev., 57:543-94 [1993] for general descriptions).

The term "PTS negative phenotype" or "PTS⁻ phenotype," as used with reference to a host cell, refers to a host cell (e.g., *E. coli*) that has a significantly impaired (i.e., non-functional) PTS system. In some embodiments, the inactivation or deletion of one or more genes encoding one or more components of the PTS system results in a portion of the PTS system becoming non-functional (e.g., a ptsG deletion). In some embodiments, the inactivation or deletion of one or more genes encoding one or more component of the PTS system results in the entire PTS system becoming non-functional (e.g., a ptsHI-crr deletion).

The term "PTS positive phenotype" or "PTS+ phenotype," as used with reference to a host cell, refers to a host cell (e.g., *E. coli*), such as *E. coli* W3110K (*E. coli* Genetic Stock Center (CGSC) strain #7167), that has a functional PTS system.

The term "glucose transporter" refers to a protein that catalyzes the transport of glucose across a cell membrane into the cytoplasm. Glucose transporters are known in the art (See e.g., Hernandez-Montalvo et al., Biotech Bioeng., 83:687-94 [2003]; and Weisser et al., J. Bacteriol., 177: 3351-54 [1995]). Glucose transport can be measured using art-known means, including but not limited to high-performance liquid chromatography (HPLC) or using isotopic substrates.

The term "xylose transporter" refers to a protein that preferentially catalyzes the transport of xylose across a cell membrane into the cytoplasm. Xylose transporters are known in the art (See e.g., Henderson, J. Bioener. Biomembr., 22:525-69 [1990]; and Henderon and Maiden, Philos. Trans. R. Soc. Lond. B Biol. Sci., 326:391-410 [1990]). Xylose transport can be measured using art-known means, including but not limited to HPLC or using isotopic substrates.

The term "symporter" refers to a transport protein that simultaneously transports two different molecules or ions across a cell membrane in the same direction.

The terms "express" and "expression" includes any step involved in the production of a polypeptide including, but not limited to, transcription, post-transcriptional modification, translation, post-translational modification, and secretion.

As used herein, the term "overexpress" is intended to encompass increasing the expression of a protein to a level greater than the cell normally produces. It is intended that the term encompass overexpression of endogenous, as well as heterologous proteins.

As used herein, the term "recombinant" refers to a polynucleotide or polypeptide that does not naturally occur in a host cell. In some embodiments, recombinant molecules contain two or more naturally-occurring sequences that are linked together in a way that does not occur naturally. In some embodiments, "recombinant cells" express genes that are not found in identical form within the native (i.e., non-recombinant) form of the cell and/or express native genes that are otherwise abnormally over-expressed, under-expressed, and/or not expressed at all due to deliberate human intervention. As used herein, "recombinant cells," as well as recombinant host cells," "recombinant microorganisms," and "recombinant fungal cells," contain at least one recombinant polynucleotide or polypeptide.

As used herein, "recombinant" used in reference to a cell or vector, refers to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. Thus, "recombinant" or "engineered" or "non-naturally occurring" when used with reference to a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level. "Recombination," "recombining" and generating a "recombined" nucleic acid generally encompass the assembly of at least two nucleic acid fragments. In some embodiments, "Recombination," "recombining," and generating a "recombined" nucleic acid also encompass the assembly of two or more nucleic acid fragments wherein the assembly gives rise to a chimeric gene.

As used herein, when used with reference to a nucleic acid or polypeptide, the term "heterologous" refers to a sequence that is not normally expressed and secreted by an organism (e.g., a wild-type organism). In some embodiments, the term encompasses a sequence that comprises two or more sub-sequences which are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature (e.g., a nucleic acid open reading frame (ORF) of the invention operatively linked to a promoter sequence inserted into an expression cassette, such as a vector).

A nucleic acid construct, nucleic acid (e.g., a polynucleotide), polypeptide, or host cell is referred to herein as "recombinant" when it is non-naturally occurring, artificial or engineered.

Reference herein to particular endogenous genes by name is for illustration and not limitation. It is understood that gene names vary from organism to organism and reference to a gene name is not intended to be limiting, but is intended to encompass homologs (i.e., which may be endogenous to a related microbial organism) and polymorphic variants. Homologs and polymorphic variants can be identified based on sequence identity and/or similar biological (e.g., enzymatic) activity. In some embodiments, the invention includes a polynucleotide or polypeptide sequence with at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% identity with the named gene or gene product. In certain embodiments, the invention includes a polynucleotide or polypeptide sequence with at least 50%, 55%, 60%, 65%, 70%, 75%, 80%, 85%, 90%, 91%, 92%, 93%, 94%, 95%, 96%, 97%, 98%, or 99% identity with the named gene or gene product.

The terms "substantial identity" and "substantially identical" refers to in the context of two nucleic acid or polypeptide sequences, refers to a sequence that has at least about 70% identity to a reference sequence. Percent identity can be any integer from about 70% to about 100% (e.g., from 70% to 100%). Two nucleic acid or polypeptide sequences that have 100% sequence identity are said to be "identical." A nucleic acid or polypeptide sequence are said to have "substantial sequence identity" to a reference sequence when the sequences have at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%, or greater sequence identity as determined using the methods described herein, such as BLAST using standard parameters as described above.

"Identity" and "percent identity," as used in the context of two or more polynucleotide or polypeptide sequences, refers to two or more sequences or sub-sequences that are the same or have a specified percentage of nucleotides or amino acid residues, respectively, that are the same. Percent identity may be determined by comparing two optimally aligned sequences over a comparison window, wherein the portion of the polynucleotide or polypeptide sequence in the comparison window may comprise additions or deletions (i.e., gaps) as compared to the reference sequence (which may also contain gaps to optimize the alignment) for alignment of the two sequences. For example, the sequence can have a percent identity of at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% over a specified region to a reference sequence when compared and aligned for maximum correspondence over a comparison window, or designated region as measured using a sequence comparison algorithms or by manual alignment and visual inspection. In some embodiments, the sequence can have a percent identity of at least 50%, 55%, 60%, 65%, 70%, 75%, 80%, 85%, 90%, 91%, 92%, 93%, 94%, 95%, 96%, 97%, 98%, or 99% over a specified region to a reference sequence when compared and aligned for maximum correspondence over a comparison window, or designated region as measured using a sequence comparison algorithms or by manual alignment and visual inspection.

Alignment of sequences for comparison can be conducted using any suitable method, including but not limited to methods such as the local homology algorithm (See e.g., Smith and Waterman, Adv. Appl. Math., 2:482 [1981]), homology alignment algorithm (See e.g., Needleman and Wunsch, J. Mol. Biol., 48:443 [1970]), the search for similarity method (See e.g., Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection (See e.g., Ausubel et al., [eds.], Current Protocols in Molecular Biology, and Supplements, John Wiley & Sons, Inc. [1995]).

Examples of algorithms that are suitable for determining percent sequence identity and sequence similarity are the BLAST and BLAST 2.0 algorithms (See e.g., Altschul et al., J. Mol. Biol., 215: 403-410 [1990]; and Altschul et al., Nucl. Acids Res., 3389-3402 [1977], respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (See, Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc Natl Acad Sci USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides over a "comparison window" to identify and compare local regions of sequence similarity.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

As used herein, "polynucleotide" refers to a polymer of deoxyribonucleotides or ribonucleotides in either single- or double-stranded form, and complements thereof.

The terms "polypeptide" and "protein" are used interchangeably herein to refer to a polymer of amino acid residues.

The terms "improved sugar utilization" and "increased sugar utilization" can refer to increasing the amount of sugar (e.g., glucose and/or xylose) consumed over a specific period of time and/or increasing the rate at which sugar (e.g., glucose and/or xylose) is consumed in a specified amount of time. In some embodiments, a host cell that has been modified as described herein (e.g., expressing one or more genes encoding one or more proteins having glucose transport activity and/or xylose transport activity) has improved sugar utilization if the amount of sugar (e.g., glucose and/or xylose) consumed by the cell over a specified period of time (e.g., over about 2, about 5, about 10, about 15, about 20, about 25, about 30, or about 35 hours) is at least about 10%, at least about 15%, at least about 20%, at least about 25%, at least about 30%, at least about 40%, or at least about 50% greater than the amount of sugar consumed over the same specified period of time for a control cell (e.g., an otherwise identical strain that has not been recombinantly modified to increase expression or activity of sugar transporters (e.g., glucose transport activity and/or xylose transport activity), such as E. coli W3110K (E. coli Genetic Stock Center (CGSC) strain #7167). In some embodiments, a host cell that has been modified as described herein (e.g., expressing one or more genes encoding one or more proteins having glucose transport activity and/or xylose transport activity) has improved sugar utilization if the amount of sugar (e.g., glucose and/or xylose) consumed by the cell over a specified period of time (e.g., over about 2, 5, 10, 15, 20, 25, 30, or 35 hours) is at least 10%, at least 15%, at least 20%, at least 25%, at least 30%, at least 40%, or at least 50% greater than the amount of sugar consumed over the same specified period of time for a control cell (e.g., an otherwise identical strain that has not been recombinantly modified to increase expression or activity of sugar transporters (e.g., glucose transport activity and/or xylose transport activity), such as E. coli W3110K (E. coli Genetic Stock Center (CGSC) strain #7167).

In some embodiments, a host cell that has been modified as described herein has improved sugar utilization if the rate at which the cell consumes a specified amount of sugar (e.g., glucose and/or xylose) is at least about 10%, at least about 15%, at least about 20%, at least about 25%, at least about 30%, at least about 40%, or at least about 50% greater than the rate for a control cell under the same culture conditions. In some embodiments, a host cell that has been modified as described herein has improved sugar utilization if the rate at which the cell consumes a specified amount of sugar (e.g., glucose and/or xylose) is at least 10%, at least 15%, at least 20%, at least 25%, at least 30%, at least 40%, or at least 50% greater than the rate for a control cell under the same culture conditions.

As used herein, a cell or strain that "co-utilizes" (or exhibits "co-utilization") of xylose and glucose refers to a cell or strain that when grown in medium containing both xylose and glucose (e.g., 1 part xylose to 2 parts glucose) consumes (ferments) both sugars simultaneously rather than, in contrast, consuming (fermenting) the glucose before consuming (fermenting) the xylose. In some embodiments, a strain that co-utilizes glucose and xylose does not exhibit significant catabolite repression of xylose consumption in the presence of glucose. In some embodiments, a strain that co-utilizes glucose and xylose does not exhibit catabolite repression of xylose consumption in the presence of glucose.

The terms "improved co-utilization" or "increased co-utilization," as used with reference to co-utilization of multiple sugars (e.g., glucose and xylose), refer to increasing the consumption of multiple sugars (e.g., glucose and xylose) by a host cell at the same time over a specific period of time and/or increasing the rate at which a specified amount of multiple sugars (e.g., glucose and xylose) are consumed by the host cell over a specified period of time. In some embodiments, a host cell that has been modified as described herein (e.g., expressing one or more genes encoding one or more proteins having glucose transport activity and/or xylose transport activity) has improved sugar co-utilization if the amount of total sugars (e.g., glucose plus xylose) consumed by the cell over a specified period of time (e.g., about 5, about 10, about 15, about 20, about 25, about 30, or about 35 hours) is at least about 10%, at least about 15%, at least about 20%, at least about 25%, at least about 30%, at least about 40%, or at least about 50% greater than the amount of total sugars (e.g., glucose plus xylose) consumed over the same specific period of time for a control cell (e.g., an otherwise identical strain in that has not been recombinantly modified to increase expression or activity of sugar transporters, e.g., E. coli W3110K (E. coli Genetic Stock Center (CGSC) strain #7167). In some embodiments, a host cell that has been modified as described herein (e.g., expressing one or more genes encoding one or more proteins having glucose transport activity and/or xylose transport activity) has improved sugar co-utilization if the amount of total sugars (e.g., glucose plus xylose) consumed by the cell over a specified period of time (e.g., about 5, 10, 15, 20, 25, 30, or 35 hours) is at least 10%, at least 15%, at least 20%, at least 25%, at least 30%, at least 40%, or at least 50% greater than the amount of total sugars (e.g., glucose plus xylose) consumed over the same specific period of time for a control cell (e.g., an otherwise identical strain in that has not been recombinantly modified to increase expression or activity of sugar transporters, e.g., E. coli W3110K (E. coli Genetic Stock Center (CGSC) strain #7167).

In some embodiments, a host cell that has been modified as described herein has improved sugar co-utilization if the rate at which a specified amount of total sugars (e.g., glucose plus xylose) is consumed by the host cell in a specified amount of time (e.g., about 5, about 10, about 15, about 20, about 25, about 30, or about 35 hours) is at least about 10%, at least about 15%, at least about 20%, at least about 25%, at least about 30%, at least about 40%, or at least about 50% faster than the rate at which the same specified amount of total sugars (e.g., glucose plus xylose) is consumed in the same specified amount of time by a control cell (e.g., an unmodified host cell of the same type). In some embodiments, a host cell that has been modified as described herein has improved sugar co-utilization if the rate at which a specified amount of total sugars (e.g., glucose plus xylose) is consumed by the host cell in a specified amount of time (e.g., about 5, 10, 15, 20, 25, 30, or 35 hours) is at least 10%, at least 15%, at least 20%, at least 25%, at least 30%, at least 40%, or at least 50% faster than the rate at which the same specified amount of total sugars (e.g., glucose plus xylose) is consumed in the same specified amount of time by a control cell (e.g., an unmodified host cell of the same type).

The terms "restoring sugar utilization" and "restoration of sugar utilization" refer to restoring the amount of sugar consumed over a specific period of time and/or the rate at which a specified amount of sugar is consumed in a specified amount of time to substantially wild-type levels. In some embodiments, a host cell that has been modified as described herein (e.g., expressing one or more genes encoding one or more proteins having glucose transport activity and/or xylose transport activity) has restored sugar utilization if the cell consumes at least about 70%, about 75%, about 80%, about 85%, about 90%, about 95%, or about 100% as much sugar in a specified amount of time as compared to a wild-type cell. In some embodiments, a host cell that has been modified as described herein (e.g., expressing one or more genes encoding one or more proteins having glucose transport activity and/or xylose transport activity) has restored sugar utilization if the cell consumes at least 70%, 75%, 80%, 85%, 90%, 95%, or 100% as much sugar in a specified amount of time as compared to a wild-type cell. In some embodiments, a host cell that has been modified as described herein has restored sugar utilization if the cell consumes sugar at a rate that is at least about 70%, about 75%, about 80%, about 85%, about 90%, about 95%, or about 100% as the rate of sugar consumption of a wild-type cell. In some embodiments, a host cell that has been modified as described herein has restored sugar utilization if the cell consumes sugar at a rate that is at least 70%, 75%, 80%, 85%, 90%, 95%, or 100% as the rate of sugar consumption of a wild-type cell.

The term "wild-type," as used with reference to a microorganism, refers to an organism (e.g., E. coli) that is naturally occurring or which has not been recombinantly modified to increase or decrease transport or utilization of specific sugars.

An amino acid or nucleotide sequence (e.g., a promoter sequence, signal peptide, terminator sequence, etc.) is "heterologous" to another sequence with which it is operably linked if the two sequences are not associated in nature. The term "heterologous," as used with reference to a sequence expressed in a microorganism, can also refer to a sequence that is not naturally occurring in the microorganism.

Nucleic acid sequences may be "introduced" into a cell by any suitable method, including but not limited to transfection, transduction, transformation. A nucleic acid sequence introduced into a eukaryotic or prokaryotic cell may be integrated into a chromosome or may be maintained in an episome.

The terms "transform" and "transformation," when used in reference to a cell, means a cell has a non-native nucleic acid sequence integrated into its genome or present as an episome (e.g., plasmid) that is maintained through multiple generations.

The term "vector" refers to a DNA construct comprising a DNA protein coding sequence. A vector may be an expression vector comprising a protein coding sequence operably linked to a suitable control sequence (i.e., promoter) capable of effecting the expression of the DNA in a suitable host.

"Operably linked" means that DNA sequence segments are arranged so that they function in concert for their intended purposes (e.g., a promoter controls transcription of a gene sequence to which it is operably linked).

A "promoter sequence" is a nucleic acid sequence that is recognized by a cell for expression of a protein coding sequence. The promoter may be any nucleic acid sequence which shows transcriptional activity in the cell of choice including mutant, truncated, hybrid, and synthetic promoters, and includes promoters from genes endogenous or exogenous (heterologous) to the host cell.

The term "culturing" refers to growing a population of microbial cells under suitable conditions in a liquid or solid medium. Most often a liquid medium is used. In some embodiments, culturing refers to the fermentative bioconversion of a substrate to an end product.

The term "contacting," as used with reference to culturing microorganisms, refers to culturing the microorganism in a medium containing a substrate (e.g., glucose and/or xylose).

In some embodiments, the carbon source for the glucose and/or xylose is derived from biomass that has been treated with various cellulose enzymes. The term "biomasss" is broadly used herein to encompasses any living or dead biological material that contains a polysaccharide substrate, including but not limited to cellulose, starch, other forms of long-chain carbohydrate polymers, and mixtures of such sources. Examples of biomass include, but are not limited to, wood, wood pulp, paper pulp, corn fiber, grain, corn grain, corn cobs, sugar cane, sugar beet, crop residues such as corn husks, corn stover, grasses, wheat, wheat straw, barley, barley straw, hay, rice, rice straw, switchgrass, waste paper, paper and pulp processing waste, woody or herbaceous plants, fruit or vegetable pulp, distillers grain, grasses, rice hulls, cotton, hemp, flax, sisal, sugar cane bagasse, sorghum, soy, components obtained from milling of grains, trees, branches, roots, leaves, wood chips, sawdust, shrubs and bushes, vegetables, fruits, and flowers and any suitable mixtures thereof. In some embodiments, the biomass comprises, but is not limited to cultivated crops (e.g., grasses, including C4 grasses, such as switch grass, cord grass, rye grass, miscanthus, reed canary grass, or any combination thereof), sugar processing residues, for example, but not limited to, bagasse (e.g., sugar cane bagasse, beet pulp [e.g., sugar beet], or a combination thereof), agricultural residues (e.g., soybean stover, corn stover, corn fiber, rice straw, sugar cane straw, rice, rice hulls, barley straw, corn cobs, wheat straw, canola straw, oat straw, oat hulls, corn fiber, hemp, flax, sisal, cotton, or any combination thereof), fruit pulp, vegetable pulp, distillers' grains, forestry biomass (e.g., wood, wood pulp, paper pulp, recycled wood pulp fiber, sawdust, hardwood, such as aspen wood, softwood, or a combination thereof). Furthermore, in some embodiments, the biomass comprises cellulosic waste material and/or forestry waste materials, including but not limited to, paper and pulp processing waste, municipal paper waste, newsprint, cardboard and the like. In some embodiments, biomass comprises one species of fiber, while in alternative embodiments, the biomass comprises a mixture of fibers that originate from different biomasses. In some embodiments, the biomass may also comprise transgenic plants that express ligninase and/or cellulase enzymes (See, e.g., US 2008/0104724 A1).

DETAILED DESCRIPTION OF THE INVENTION

The present invention provides host cells having improved sugar utilization or co-utilization, methods of producing host cells having improved sugar utilization or co-utilization, and methods of using host cells having improved sugar utilization or co-utilization.

As described herein, including in the Examples, the present invention shows that a putative sugar transport gene product from *Zymomonas mobilis* subsp. *pomaceae*, in combination with the glucokinase (glk) gene product from *E. coli*, restores glucose transport in a PTS⁻ cell line. Thus, in one aspect the present invention relates to a host cell (e.g., *E. coli*) that has been modified to have restored glucose utilization, relative to a control host cell from which the modified host cell is derived, wherein the cell has been modified to express a gene encoding a polypeptide that is substantially identical to the *Z. mobilis* subsp. *pomaceae* putative sugar transport gene. Furthermore, it has been demonstrated that PTS⁻ host cells expressing the *Z. mobilis* subsp. *pomaceae* putative sugar transport gene and the xylose transporter XylE have improved co-utilization of glucose and xylose as compared to a wild-type cell line. Thus, in another aspect the present invention relates to a host cell that has been modified to have improved glucose and xylose co-utilization, wherein the host cell has been modified to express a first gene encoding a polypeptide that is substantially identical to the *Z. mobilis* subsp. *pomaceae* putative sugar transport gene and a second gene encoding a polypeptide having xylose transport activity. The present invention provides these and other host cells having improved sugar utilization or co-utilization, methods of producing host cells having improved sugar utilization or co-utilization, and methods of using host cells having improved sugar utilization or co-utilization.

In one aspect, the present invention relates to cells that have improved sugar utilization (e.g., improved glucose utilization and/or improved xylose utilization) or improved co-utilization of glucose and xylose. In some embodiments, the present invention provides host cells or strains that may be modified to improve sugar utilization. In some embodiments, these host cells or strains are any organism capable of using a phosphoenolpyruvate-dependent phosphotransferase transfer (PTS) system for carbohydrate transport. In some other embodiments, host cells or strains that may be modified to improve sugar utilization by the methods encompassed by the instant invention do not use the PTS system.

Suitable host cells include, but are not limited to, prokaryotes or other microorganisms. In some embodiments, the host cell belongs to the genus *Agrobacterium, Bacillus, Brevibacterium, Clostridium, Corynebacterium, Escherichia, Erwinia, Klebsiella, Lactobacillus, Lactococcus, Pantoea, Pseudomonas, Staphylococcus, Salmonella, Streptococcus, Streptomyces, Vibrio,* or *Zymomonas*. In some embodiments, the host cell is a species of *Escherichia* (e.g., *E. coli*).

In some embodiments, a host cell to be modified to improve sugar utilization has a PTS+ phenotype. In some embodiments, a host cell to be modified to improve sugar utilization has a PTS⁻ phenotype, i.e., has a deletion or inactivation of one or more genes that results in the inactivation at least one part of the PTS system or of the entire PTS system. In some embodiments, the PTS system is inactivated by disrupting one or more of the genes encoding phosphocarrier protein (ptsH), phosphoenolpyruvate-protein phosphotransferase (ptsI), and glucose-specific IIA component (crr). In some embodiments, a PTS⁻ host cell comprises a deletion that inactivates part of the PTS system (e.g., ΔptsG). In some embodiments, a PTS⁻ host cell comprises a deletion that inactivates the entire PTS system (e.g., ΔptsHI-crr). Methods for gene disruption in microorganisms are well known in the art (See e.g., Gosset, Microb. Cell Fact., 4:14 [2005]; Chatterjee et al., Appl. Environ. Microbiol., 67:148 [2001]; and De Reuse and Danchin, J. Bacteriol., 170:3827-37 [1988]). The particular method used to inactivate part or all of the PTS system is not critical to the invention. It is also not intended that the present invention be limited to the specific cells described herein, as other suitable cells find use in the present invention.

It will be appreciated that, consistent with terminology standard in the art, reference to, for example, "modifying a host cell" means that a cell or population of cells and their progeny are modified and does not refer to or require that a single or individual cell be modified. For example, a process in which a first gene is introduced into a population (culture) of E. coli cells, subpopulations are selected and cultured for many generations, and a second gene is introduced into the population containing the first gene can be described as "introducing the first gene and second gene into a host cell."

For illustration, and not limitation, E. coli cells of the invention that may be used in the practice of the invention include the following:

PTS Negative, Glucose Positive Strains.

In some embodiments, the strain comprises a ptsG deletion or inactivation and/or a deletion or inactivation of one or more of the ptsH, ptsI, and crr genes. In some embodiments, the PTS negative, glucose positive strain overexpresses a gene encoding a polypeptide having glucose transport activity. In some embodiments, the polypeptide having glucose transport activity is Pom (SEQ ID NO:2). In some embodiments, the polypeptide having glucose transport activity is a Pom homolog. In some embodiments, the polypeptide having glucose transport activity has at least about 85%, about 90%, about 91%, about 92%, about 93%, about 94%, about 95%, about 96%, about 97%, about 98%, about 99%, or about 100% sequence identity to the amino acid sequence of Pom (SEQ ID NO:2). In some embodiments, the polypeptide having glucose transport activity is a Pom homolog. In some embodiments, the polypeptide having glucose transport activity has at least 85%, 90%, 91%, 92%, 93%, 94%, 95%, 96%, 97%, 98%, 99%, or higher sequence identity to the amino acid sequence of Pom (SEQ ID NO:2). In some embodiments, the E. coli strain comprises a deletion or inactivation of ptsH, ptsI, and crr and further comprises a gene encoding Pom (SEQ ID NO:2) operably linked to a constitutive promoter. In some embodiments, the strain further comprises a gene encoding a glucokinase. In some embodiments, the E. coli strain is W3110K-ΔptsHI-crr::Km—insH11::pG-Pom-glk, described below in Example 5.

PTS Negative, Xylose Positive Strains.

In some embodiments, the PTS negative, xylose positive strain comprises a ptsG deletion or inactivation and/or a deletion or inactivation of one or more of the ptsH, ptsI, and crr genes. In some embodiments, the PTS negative, xylose positive strain overexpresses a gene encoding a polypeptide having xylose transport activity. In some embodiments, the polypeptide having xylose transport activity is a xylose symporter (e.g., xylE). In some embodiments, the polypeptide having xylose transport activity is a xylE homolog. In some embodiments, the E. coli strain comprises a deletion or inactivation of ptsH, ptsI, and crr and further comprises a gene encoding XylE operably linked to a constitutive promoter. In some embodiments, the strain further comprises a deletion or inactivation of an endogenous xylose transport protein (e.g., a xylose ABC transporter, such as XylFGH). In some embodiments, the strain further comprises a xylAB gene under the control of a constitutive promoter. In some embodiments, the E. coli strain is W3110K-ΔptsHI-crr::Km—ΔxylFGH::pAB-pE-xylE, described below in Example 7.

PTS Negative, Glucose and Xylose Co-Utilization Strains.

In some embodiments, the strain comprises a ptsG deletion or inactivation and/or a deletion or inactivation of one or more of the ptsH, ptsI, and crr genes. In some embodiments, the PTS negative, glucose and xylose positive strain overexpresses a gene encoding a polypeptide having glucose transport activity and a gene encoding a polypeptide having xylose transport activity. In some embodiments, the polypeptide having glucose transport activity is Pom (SEQ ID NO:2). In some embodiments, the polypeptide having glucose transport activity is a Pom homolog. In some embodiments, the polypeptide having glucose transport activity has at least about 85%, about 90%, about 91%, about 92%, about 93%, about 94%, about 95%, about 96%, about 97%, about 98%, about 99%, or about 100% sequence identity to the amino acid sequence of Pom (SEQ ID NO:2). In some embodiments, the polypeptide having glucose transport activity is a Pom homolog. In some embodiments, the polypeptide having glucose transport activity has at least 85%, 90%, 91%, 92%, 93%, 94%, 95%, 96%, 97%, 98%, 99%, or higher sequence identity to the amino acid sequence of Pom (SEQ ID NO:2). In some embodiments, the polypeptide having xylose transport activity is a xylose symporter (e.g., xylE).

In some embodiments, the polypeptide having xylose transport activity is a xylE homolog. In some embodiments, the E. coli strain further comprises a deletion or inactivation of ptsH, ptsI, and crr, and further comprises a first gene encoding Pom (SEQ ID NO:1) operably linked to a constitutive promoter and a second gene encoding XylE operably linked to a constitutive promoter. In some embodiments, the strain further comprises a deletion or inactivation of an endogenous xylose transport protein (e.g., a xylose ABC transporter, such as XylFGH). In some embodiments, the E. coli strain is W3110K-ΔptsHI-crr::Km—insH11::pG-Pom-glk—ΔxylFGH::pAB-pE-xylE, described below in Example 8.

PTS Positive, Glucose and Xylose Co-Utilization Strains.

In some embodiments, the strain overexpresses a gene encoding a polypeptide having xylose transport activity. In some embodiments, the polypeptide having xylose transport activity is a xylose symporter (e.g., xylE). In some embodiments, the polypeptide having xylose transport activity is a xylE homolog. In some embodiments, the E. coli strain comprises a gene encoding XylE operably linked to a constitutive promoter. In some embodiments, the strain further comprises a deletion or inactivation of an endogenous xylose transport protein (e.g., a xylose ABC transporter, such as XylFGH). In some embodiments, the strain further comprises a xylAB gene under the control of a constitutive promoter. In some embodiments, the E. coli strain is W3110K-ΔxylFGH::pAB-pE-xylE, described below in Example 9.

In some embodiments, a cell of the present invention having improved utilization of glucose or xylose and/or improved co-utilization of glucose and xylose has a PTS− phenotype. As described above, deleting all or part of the PTS system in a host cell, such as an E. coli cell, impairs the ability of the cell to utilize glucose. Moreover, deletion of the entire PTS system impairs the ability of the cell to utilize other sugars, such as xylose and arabinose. Therefore, in order to restore sugar utilization to the cell, it is necessary to add back one or more sugar transporters to the cell.

In some embodiments, the present invention provides host cells expressing a gene encoding a glucose transport protein, wherein the cells have improved glucose utilization. As described herein in the Examples section, a gene product from *Zymomonas mobilis* subsp. *pomaceae* has been identified as having homology to a known glucose transporter, the ZM4 glf gene product. As shown in FIG. 1, the putative sugar transporter from *Z. mobilis* subsp. *pomaceae* ("Pom", SEQ ID NO:2) has 85% amino acid identity to the ZM4 glf gene product (SEQ ID NO:3) as determined by amino acid alignment. The Pom gene was co-expressed in a PTS⁻ cell line (a ptsHI-crr deletion) with the glk gene product from *E. coli* and was shown to restore glucose transport in the cell line, as measured by cell growth and total glucose consumption over a 35 hour time course (See, FIG. 2). Thus, in some embodiments, the host cells have a PTS⁻ phenotype and exhibit improved glucose utilization relative to a control cell (e.g., a PTS⁻ host cell of the same type in which the gene encoding the glucose transport protein has not been expressed).

In some embodiments, the host cell has been modified to express a gene encoding a polypeptide having glucose transport activity, wherein the polypeptide has at least 85%, 90%, 91%, 92%, 93%, 94%, 95%, 96%, 97%, 98%, 99%, or higher sequence identity to the amino acid sequence of the Pom gene product (SEQ ID NO:2). In some embodiments, the polypeptide has the amino acid sequence of SEQ ID NO:2. In some embodiments, the gene encoding the polypeptide having glucose transport activity is operably linked to a heterologous promoter.

The capacity of a transporter to enable the movement of glucose into a cell, referred to as "glucose transport activity," can be measured by methods known in the art, including high-performance liquid chromatography (HPLC) or by using isotopic substrates. In some embodiments, a polypeptide (e.g., Pom or a Pom homolog) has glucose transport activity if the polypeptide (e.g., Pom or a Pom homolog), when expressed in *E. coli* as described for FIG. 2, enables the consumption of at least 50%, at least 60%, at least 70%, at least 80%, at least 90%, at least 100% or more of the amount of glucose that is consumed by a wild-type *E. coli* cell in the same time (e.g., in a 5, 10, 15, 20, 25, 30, or 35 hour time period). In some embodiments, a polypeptide (e.g., Pom or a Pom homolog) has glucose transport activity if the polypeptide (e.g., Pom or a Pom homolog), when expressed in *E. coli* as described for FIG. 2, enables the consumption of glucose at a rate that is at least 50%, at least 60%, at least 70%, at least 80%, at least 90%, at least 100% or more of glucose consumption rate for a wild-type *E. coli* cell over the same time period (e.g., in a 5, 10, 15, 20, 25, 30, or 35 hour time period).

In some embodiments, the host cell is further modified to express a gene encoding a glucokinase (glk). In some embodiments, the gene encoding glucokinase is endogenous to the host cell. In some embodiments, the gene encoding glucokinase is exogenous or heterologous to the host cell. In some embodiments, the gene encoding glucokinase is from *E. coli*. Suitable glk genes for use in modifying the host cell include any glk genes known in the art (See, e.g., Hernandez-Montalvo et al., Biotechnol. Bioeng., 83:687-94 [2003], and Snoep et al., J. Bacteriol. 176:2133-35 [1994]). One of skill in the art can readily identify glk gene sequences for use in the present invention. In some embodiments, the glk gene is operably linked to a heterologous promoter.

In some embodiments, one or more PTS genes are deleted or inactivated from the host cell prior to the expression in the host cell of the gene encoding a polypeptide having glucose transport activity. In some embodiments, a host cell is modified to express the gene encoding a polypeptide having glucose transport activity prior to the deletion or inactivation of one or more PTS genes in the host cell.

In some embodiments, host cells that are modified as described herein (e.g., a PTS⁻ host cell expressing a gene encoding a polypeptide having glucose transport activity as described herein, and optionally further expressing a gene encoding glucokinase) exhibit restored or increased glucose utilization. In some embodiments, the level of glucose utilization (e.g., the amount of glucose consumed over a specific period of time or the speed at which a specified amount of glucose is consumed in a specified amount of time) in the modified host cell is restored to wild-type levels (e.g., the level of a PTS+ cell of the same strain which has not been modified to express a gene encoding a polypeptide having glucose transport activity). In some embodiments, the amount of glucose consumed over a specific period of time (e.g., about 5, 10, 15, 20, 25, 30, or 35 hours) for a modified host cell is at least 10%, at least 15%, at least 20%, at least 25%, at least 30%, at least 40%, or at least 50% greater than the amount of glucose consumed over the same specific period of time for a wild-type cell (e.g., a PTS+ cell of the same strain which has not been modified to express a gene encoding a polypeptide having glucose transport activity). In some embodiments, the speed at which a specified amount of glucose is consumed in a specified amount of time (e.g., about 5, 10, 15, 20, 25, 30, or 35 hours) is at least 10%, at least 15%, at least 20%, at least 25%, at least 30%, at least 40%, or at least 50% faster than the speed at which the same specified amount of glucose is consumed in the same specified amount of time for the wild-type cell. Glucose consumption can be determined by methods described in the Examples (e.g., Examples 10, 11, 12, and 13) and/or using any other suitable methods known in the art.

In some embodiments, the present invention provides host cells expressing a gene encoding a xylose transport protein, wherein the cells have improved xylose utilization. In some embodiments, the host cell having improved xylose utilization has a PTS⁻ phenotype. In some embodiments, the host cell has been modified to express a gene encoding a polypeptide having xylose transport activity. Xylose transporter genes are known in the art. In some embodiments, the polypeptide having xylose transport activity is a xylose symporter (e.g., xylE). In some embodiments, the gene encoding the xylose transporter is an *E. coli* xylE gene. In some embodiments, the xylose transporter is a homolog of *E. coli* xylE. In some embodiments, the xylose transporter gene (e.g., the xylE gene), is operably linked to a heterologous promoter.

In some embodiments, the host cell is further modified to delete or inactivate an endogenous xylose transport protein and/or replace the endogenous xylose transport protein with a xylose symporter gene (e.g., a xylE gene), as described herein. In some embodiments, the method comprises replacing an endogenous ABC transporter gene (e.g., a gene encoding the xylFGH transporter) with a xylose symporter gene (e.g., a gene encoding xylE).

In some embodiments, the host cell is further modified to replace a native promoter of one or more endogenous xylose metabolism gene(s) with a promoter not associated with the gene(s) in nature. In some cases the promoter is heterologous to the host cell (i.e., from a different species). In some cases the promoter is a constitutive promoter. In some cases the promoter is a non-constitutive promoter. In some embodiments, the promoter is synthetic (e.g., derived from a promoter library; See e.g., Rud et al., Microbiol., 152:

1011-19 [2006], the disclosure of which is herein incorporated by reference in its entirety). In some embodiments, the endogenous xylose metabolism gene is xylAB and the native promoter is replaced with a constitutive promoter or a synthetic promoter (e.g., derived from a promoter library).

In some embodiments, one or more PTS genes are deleted or inactivated from the host cell prior to the expression in the host cell of the gene encoding a polypeptide having xylose transport activity. In some embodiments, a host cell is modified to express the gene encoding a polypeptide having xylose transport activity prior to the deletion or inactivation of one or more PTS genes in the host cell.

In some embodiments, host cells that are modified as described herein (e.g., a PTS⁻ host cell expressing a gene encoding a xylose symporter as described herein, and optionally further comprising a deleted or inactivated endogenous xylose ABC transporter) exhibit restored or increased xylose utilization. In some embodiments, the level of xylose utilization (e.g., the amount of xylose consumed over a specific period of time or the speed at which a specified amount of xylose is consumed in a specified amount of time) in the modified host cell is restored to wild-type levels (e.g., the level of a PTS+ cell of the same strain which has not been modified to express a gene encoding a xylose transport protein). In some embodiments, the amount of xylose consumed over a specific period of time (e.g., about 5, 10, 15, 20, 25, 30, or 35 hours) for a modified host cell is at least 10%, at least 15%, at least 20%, at least 25%, at least 30%, at least 40%, or at least 50% greater than the amount of xylose consumed over the same specific period of time for a wild-type cell (e.g., a PTS+ cell of the same strain which has not been modified to express a gene encoding a xylose transport protein). In some embodiments, the speed at which a specified amount of xylose is consumed in a specified amount of time (e.g., about 5, 10, 15, 20, 25, 30, or 35 hours) is at least 10%, at least 15%, at least 20%, at least 25%, at least 30%, at least 40%, or at least 50% faster than the speed at which the same specified amount of xylose is consumed in the same specified amount of time for the wild-type cell. Xylose consumption can be determined by methods described in the Examples (e.g., Examples 10, 12, and 13) and/or using any other methods known in the art.

In some yet additional embodiments, the present invention provides host cells expressing a first gene encoding a polypeptide having glucose transport activity and a second gene encoding a xylose transport protein, wherein the cells have improved glucose and xylose co-utilization. In some embodiments, the host cell having improved glucose and xylose co-utilization has a PTS⁻ phenotype. In some embodiments, the host cell has been modified to express a first gene that encodes a polypeptide having glucose transport activity and a second gene encoding a polypeptide having xylose transport activity. In some embodiments, the first gene encodes a polypeptide having at least 85%, 90%, 91%, 92%, 93%, 94%, 95%, 96%, 97%, 98%, 99%, or higher sequence identity to the amino acid sequence of the Pom gene product (SEQ ID NO:2). In some embodiments, the first gene encodes a polypeptide having the amino acid sequence of SEQ ID NO:2. In some embodiments, the polypeptide having xylose transport activity is a xylose symporter (e.g., xylE). In some embodiments, the polypeptide having xylose transport activity is a homolog of *E. coli* xylE. In some embodiments, the first gene encoding the polypeptide having glucose transport activity (e.g., Pom or a Pom homolog) and/or the second gene encoding a xylose transporter (e.g., xylE) is operably linked to a heterologous promoter.

In some embodiments, the host cell is further modified to express a gene encoding a glucokinase (glk). In some embodiments, the gene encoding glucokinase is endogenous to the host cell. In some embodiments, the gene encoding glucokinase is exogenous or heterologous to the host cell. In some embodiments, the gene encoding glucokinase is from *E. coli*. In some embodiments, the glk gene is operably linked to a heterologous promoter.

In some embodiments, the host cell is further modified to delete or inactivate an endogenous xylose transport protein and/or replace the endogenous xylose transport protein with a xylose symporter gene (e.g., a xylE gene), as described herein. In some embodiments, the method comprises replacing an endogenous ABC transporter gene (e.g., a gene encoding the xylFGH transporter) with a xylose symporter gene (e.g., a gene encoding xylE).

In some embodiments, the host cell is further modified to replace a native promoter of one or more endogenous xylose metabolism gene(s) with a promoter not associated with the gene(s) in nature. In some cases the promoter is heterologous to the host cell (i.e., from a different species). In some cases the promoter is a constitutive promoter. In some cases the promoter is a non-constitutive promoter. In some embodiments, the constitutive or non-constitutive promoter is synthetic. In some embodiments, the endogenous xylose metabolism gene is xylAB and the native promoter is replaced with a constitutive promoter or a synthetic promoter.

In some embodiments, one or more PTS genes are deleted or inactivated from the host cell prior to the expression in the host cell of the first gene encoding a polypeptide having glucose transport activity and the second gene encoding a polypeptide xylose transport activity. In some embodiments, a host cell is modified to express the first gene encoding a polypeptide having glucose transport activity and/or the second gene encoding a polypeptide having xylose transport activity prior to the deletion or inactivation of one or more PTS genes in the host cell.

In some embodiments, host cells that are modified as described herein (e.g., a PTS⁻ host cell expressing a first gene encoding a polypeptide having glucose transport activity as described herein and a second gene encoding a xylose transport protein as described herein, and optionally expressing a gene encoding glucokinase and/or comprising a deleted or inactivated endogenous xylose ABC transporter) exhibit increased glucose and xylose co-utilization. In some embodiments, glucose and xylose co-utilization (e.g., the amount of total glucose plus xylose consumed over a specific period of time or the speed at which a specified amount of total glucose plus xylose is consumed in a specified amount of time) in the modified host cell is increased by at least about 10%, at least 15%, at least 20%, at least 25%, at least 30%, at least 40%, or at least 50% greater than the amount of glucose consumed over the same specific period of time for a wild-type cell (e.g., a PTS+ cell of the same strain which has not been modified to express a first gene encoding a polypeptide having glucose transport activity or a second gene encoding a xylose transport protein). In some embodiments, the amount of total glucose plus xylose consumed over a specific period of time (e.g., about 5, 10, 15, 20, 25, 30, or 35 hours) for a modified host cell is at least 10%, at least 15%, at least 20%, at least 25%, at least 30%, at least 40%, or at least 50% greater than the amount of total glucose plus xylose consumed over the same specific period of time for the wild-type cell. In some embodiments, the speed at which a specified amount of total glucose plus xylose is consumed in a specified amount of time (e.g., about 5, 10, 15, 20, 25, 30, or 35 hours) is at least 10%, at least 15%, at least 20%, at least 25%, at least 30%, at least 40%, or at least 50% faster than the speed at which the same specified amount of total glucose plus xylose is consumed in the same specified amount of time for the wild-type cell. Glucose and xylose consumption can be determined by methods described in the Examples (e.g., Examples 10, 11, 12, and 13) and/or using any other methods known in the art.

In still additional embodiments, the present invention provides host cells having an intact (i.e., functioning) PTS system and having improved the co-utilization of glucose and xylose. As described above, a host cell having an intact PTS system preferentially consumes glucose when glucose is present, even in the presence of other sugars, and represses metabolic pathways that allow assimilation of non-glucose carbon sources. In some embodiments, a host cell a PTS+ phenotype is modified to express a gene encoding a polypeptide having xylose transport activity. In some embodiments, the polypeptide having xylose transport activity is a xylose symporter (e.g., xylE). In some embodiments, the gene encoding the xylose transporter is an *E. coli* xylE gene. In some embodiments, the xylose transporter is a homolog of *E. coli* xylE. In some embodiments, the xylose transporter gene (e.g., xylE gene) is operably linked to a heterologous promoter.

In some embodiments, the host cell is further modified to delete or inactivate an endogenous xylose transport protein and/or replace the endogenous xylose transport protein with a xylose symporter gene (e.g., a xylE gene), as described herein. In some embodiments, the method comprises replacing an endogenous ABC transporter gene (e.g., a gene encoding the xylFGH transporter) with a xylose symporter gene (e.g., a gene encoding xylE).

In some embodiments, the host cell is further modified to replace a native promoter of one or more endogenous xylose metabolism gene(s) with a constitutive promoter. In some cases the promoter is heterologous to the host cell (i.e., from a different species). In some cases the promoter is a constitutive promoter. In some cases the promoter is a non-constitutive promoter. In some embodiments, the promoter is synthetic (e.g., derived from a promoter library). In some embodiments, the endogenous xylose metabolism gene is xylAB and the native promoter is replaced with a constitutive promoter or a synthetic promoter (e.g., derived from a promoter library).

In some embodiments, host cells that are modified as described herein (e.g., a PTS+ host cell expressing a xylose transport protein as described herein, and optionally comprising a deleted or inactivated endogenous xylose ABC transporter) exhibit increased glucose and xylose co-utilization. In some embodiments, glucose and xylose co-utilization (e.g., the amount of total glucose plus xylose consumed over a specific period of time or the speed at which a specified amount of total glucose plus xylose is consumed in a specified amount of time) in the modified host cell is increased by at least about 10%, at least 15%, at least 20%, at least 25%, at least 30%, at least 40%, or at least 50% greater than the amount of glucose consumed over the same specific period of time for a wild-type cell (e.g., an unmodified PTS+ cell of the same strain). In some embodiments, the amount of total glucose plus xylose consumed over a specific period of time (e.g., about 5, 10, 15, 20, 25, 30, or 35 hours) for a modified host cell is at least 10%, at least 15%, at least 20%, at least 25%, at least 30%, at least 40%, or at least 50% greater than the amount of total glucose plus xylose consumed over the same specific period of time for the wild-type cell. In some embodiments, the speed at which a specified amount of total glucose plus xylose is consumed in a specified amount of time (e.g., about 5, 10, 15, 20, 25, 30, or 35 hours) is at least 10%, at least 15%, at least 20%, at least 25%, at least 30%, at least 40%, or at least 50% faster than the speed at which the same specified amount of total glucose plus xylose is consumed in the same specified amount of time for the wild-type cell. Glucose and xylose consumption can be determined by methods described in the Examples (e.g., Examples 10, 11, 12, and 13) and/or using any other methods known in the art.

The present invention also provides methods of making host cells having improved glucose utilization, xylose utilization, and/or glucose plus xylose co-utilization. In some embodiments, the invention relates to methods of making PTS⁻ host cells having improved glucose utilization. In some embodiments, the method comprises: modifying the host cell to express a gene encoding a polypeptide having glucose transport activity, wherein the gene is operably linked to a heterologous promoter, and wherein the polypeptide having glucose transport activity has at least 85% sequence identity to the amino acid sequence of SEQ ID NO:2. In some embodiments, the polypeptide has the amino acid sequence of SEQ ID NO:2.

In some embodiments, the present invention provides methods of making PTS⁻ host cells having improved xylose utilization. In some embodiments, the method comprises: modifying the host cell to express a gene encoding a polypeptide having xylose transport activity, wherein the gene is operably linked to a heterologous promoter. In some embodiments, the polypeptide having xylose transport activity is a xylose symporter (e.g., xylE).

In some embodiments, the invention provides methods of making PTS⁻ host cells having improved glucose and xylose co-utilization. In some embodiments, the method comprises: modifying the host cell to express (i) a first gene encoding a polypeptide having glucose transport activity, wherein the gene is operably linked to a first heterologous promoter, and wherein the polypeptide having glucose transport activity has at least 85% sequence identity to the amino acid sequence of SEQ ID NO:2; and (ii) second gene encoding a polypeptide having xylose transport activity, wherein the second gene is operably linked to a second heterologous promoter. In some embodiments, the polypeptide having glucose transport activity has the amino acid sequence of SEQ ID NO:2. In some embodiments, the polypeptide having xylose transport activity is a xylose symporter (e.g., xylE).

In some embodiments, the invention provides methods of making PTS+ host cells having improved glucose and xylose co-utilization. In some embodiments, the method comprises: modifying the host cell to express a gene encoding a polypeptide having xylose transport activity, wherein the gene is operably linked to a heterologous promoter. In some embodiments, the polypeptide having xylose transport activity is a xylose symporter (e.g., xylE).

In various embodiments, the host cells (PTS⁻ or PTS+) that have been modified to have improved glucose utilization, xylose utilization, and/or glucose plus xylose co-utilization contain one or more exogenous genes (e.g., glucose transporter genes and/or xylose transporter genes) operably linked to a heterologous promoter that is functional in the host cell. In some embodiments, the promoter is a promoter associated in nature with a different host cell gene (e.g., an *E. coli* lac promoter operably linked to a glucose transport gene and/or a xylose transport gene). In some embodiments, the promoter is heterologous to the host cell (e.g., a T7 promoter in an *E. coli* host). In some embodiments, the promoter is synthetic (e.g., derived from a promoter library).

In some embodiments, expression of one or more exogenous genes (e.g., glucose transporter genes and/or xylose transporter genes) is accomplished by introducing the exogenous gene into the organism on an episomal plasmid. In some embodiments, expression of one or more exogenous genes (e.g., glucose transporter genes and/or xylose transporter genes) is accomplished by integrating the gene into the genome of the host cell. Integration of the exogenous gene into the genome of the host cell has various advantages over the use of plasmids, including but not limited to less variation in protein expression and the potential for high levels of expression by introducing multiple copies of a single gene (e.g., two, three, four, five, or more copies of the exogenous gene). The incorporation of an exogenous gene can be accomplished by techniques well known in the art.

The promoter sequence is a nucleic acid sequence that is recognized by a host cell for expression of a polynucleotide, such as a polynucleotide containing the coding region. Generally, the promoter sequence contains transcriptional control sequences, which mediate expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell. In some embodiments, the promoter may be a weak, medium, or strong promoter. Methods for the isolation, identification and manipulation of promoters of varying strengths are available in or readily adapted from the art (See e.g., Nevoigt et al., Appl. Environ. Microbiol., 72:5266-5273 [2006], the disclosure of which is herein incorporated by reference in its entirety. In some embodiments, the promoter is a synthetic promoter.

In some embodiments, the promoter is a constitutive promoter. In some embodiments, the promoter is a constitutive promoter library (e.g., a constitutive synthetic promoter library). Methods of generating or manipulating synthetic promoter libraries are known in the art (See e.g, Rud et al., Microbiol., 152:1011-1019 [2006], the disclosure of which is herein incorporated by reference in its entirety).

Expression vectors may be used to transform a host cell of the present invention with a gene encoding a polypeptide having glucose transport activity and/or a gene encoding a glucokinase protein and/or a gene encoding a xylose transport protein. A recombinant expression vector can be any vector (e.g., a plasmid or a virus), that can be manipulated by recombinant DNA techniques to facilitate expression of the exogenous gene in the microbial organism. In some embodiments, the expression vector is stably integrated into the chromosome of the microbial organism. In other embodiments, the expression vector is an extrachromosomal replicative DNA molecule (e.g., a linear or closed circular plasmid), that is found either in low copy number (e.g., from about 1 to about 10 copies per genome equivalent) or in high copy number (e.g., more than about 10 copies per genome equivalent).

Expression vectors for expressing the one or more exogenous genes are commercially available (e.g., from Sigma-Aldrich Chemicals, St. Louis, Mo. and Stratagene, La Jolla, Calif.). In some embodiments, examples of suitable expression vectors are plasmids which are derived from pBR322 (Gibco BRL), pUC (Gibco BRL), pREP4, pCEP4 (Invitrogen) or pPoly (See e.g., Lathe et al., Gene 57:193-201 [1987]).

In some embodiments, wherein more than one exogenous gene is to be expressed in the host cell, separate expression vector are used for each exogenous gene to be expressed. In other embodiments, the same expression vector is used for two or more exogenous genes to be expressed, and the expression of each gene is independently regulated by a different promoter.

Expression of the exogenous gene may be enhanced by also incorporating transcription terminators, leader sequences, polyadenylation sequences, secretory signals, propeptide coding regions, regulatory sequences, and/or selectable markers as would be apparent to one of skill in the art. The choice of appropriate control sequences for use in the polynucleotide constructs of the present disclosure is within the skill in the art and in various embodiments is dependent on the recombinant host cell used.

Methods, reagents, and tools for transforming and culturing the host cells described herein are known in the art and can be readily determined by those skilled in the art. General methods, reagents and tools for transforming (e.g., bacteria) can be found, for example, in Sambrook et al., *Molecular Cloning: A Laboratory Manual*, $3^{rd}$ ed., Cold Spring Harbor Laboratory Press, New York [2001]. Many references are available for the culture and production of many cells, including cells of bacterial, plant, animal (especially mammalian) and archebacterial origin (See e.g., Sambrook, Ausubel, and Berger (all supra), as well as Freshney *Culture of Animal Cells, a Manual of Basic Technique*, $3^{rd}$ ed., Wiley-Liss, New York [1994] and the references cited therein; Doyle and Griffiths, *Mammalian Cell Culture: Essential Techniques* John Wiley and Sons, NY [1997]; Humason (1979) *Animal Tissue Techniques*, $4^{th}$ ed., W.H. Freeman and Company [1979]; and Ricciardelli et al., *In Vitro Cell Dev. Biol.* 25:1016-1024 [1989], all of which are incorporated herein by reference). Culture conditions, such as temperature, pH and the like, will be apparent to those skilled in the art.

It will be appreciated that cells various strategies and methods can be used to modify cells and the invention is not limited to a particular method. For illustration, a PTS$^-$, Pom+, xylE+ cell could be made by introducing Pom$^+$ and xylE$^+$ (in either order or simultaneously) into a PTS+ cell and then knocking out PTS function or, equivalently, could be made by introducing Pom$^+$ and xylE$^+$ (in either order or simultaneously) into a PTS$^-$ cell. It is well within the ability of one of ordinary skill in the art guided by this disclosure to produce cells of the invention using a variety of strategies.

In addition to the modifications specifically described above, host cells of the invention may have any number of other modifications to provide desirable properties, including, for example, drug resistance. In particular, many recombinant *E. coli* or other bacterial or microbial cells have been engineered to express a product of interest, and or a protein or proteins of interest. It is contemplated that the cells of the invention, which are engineered to co-utilize glucose and xylose, will find use in the production of many end-products. These end-products include glycerol; acetone; alcohols (e.g., ethanol, butanol, propanol, isopropanol, etc.); diols (e.g., 1,3-propanediol, butanediol, etc.); amino acids (e.g., lysine, glutamine, glycine, etc.); organic acids (e.g., lactic acid, succinate, ascorbic acid, adipic acid, etc.); vitamins; drugs and drug precursors; hormones; antibiotics; hydrocarbons (e.g., fatty alcohols and fatty alcohol derivatives, waxes, olefins, etc.); acrylic acid; butadiene; and other chemicals. In particular, the host cells described herein can be used to make any product that recombinant E. coli is known to make and it is not intended that the present invention be limited to any particular end-product.

EXPERIMENTAL

The present invention is described in further detail in the following Examples, which are not in any way intended to limit the scope of the invention as claimed.

In the experimental disclosure below, the following abbreviations apply: ppm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); ul, uL, μL, and μl (microliter); cm (centimeters); mm (millimeters); um and μm (micrometers); sec. and " " " (i.e., quote symbol) (seconds); min(s) and " " " " (i.e., an apostrophe) (minute(s)); h(s) and hr(s) (hour(s)); U (units); MW (molecular weight); rpm (rotations per minute); rt (room temperature); ° C. (degrees Centigrade); DNA (deoxyribonucleic acid); RNA (ribonucleic acid); HPLC (high pressure liquid chromatography); RID (refractive index detector); LB (Luria-Bertani); (Promega (Promega, Corp, Madison, Wis.); Fermentas (Fermentas, Glen Burnie, Md.); NEB and New England BioLabs (New England BioLabs, Iswich, Mass.); GenScript (GenScript USA Inc., Piscataway, N.J.); Invitrogen (Invitrogen, Life Technologies, Grand Island, N.Y.); Affymetrix (Affymetrix, Inc., Santa Clara, Calif.); Difco (Difco Laboratories, BD Diagnostic Systems, Detroit, Mich.); Sigma-Aldrich (Sigma-Aldrich, St. Louis, Mo.); ATCC (American Type Culture Collection, Manassas, Va.); Sartorius (Sartorius Corp., Bohemia, N.Y.); Bio-Rad (Bio-Rad Laboratories, Hercules, Calif.); and Agilent (Agilent Technologies, Inc., Santa Clara, Calif.).

The following sequence is the cDNA encoding putative sugar transporter from *Zymomonas mobilis* subspecies *pomaceae*:

(SEQ ID NO: 1)
ATGAGTTCAGAAAGTAGTCAAGGTCTAGTCACGCGACTAGCCTTAATTGC
CGCCATTGGCGGTCTACTATTTGGTTACGATTCAGCCGTTATTGCTGCGA
TCGGTATACCGGTTGATATTAACTTTATTGGTCCCCGCCATCTGTCAGCT
ACCGCTGCCGCCTCCCTTTCAGGGATGGTGGTTGTTGCTGTCTTGGCAGG
TTGTGTTGTTGGTTCATTAATTTCCGGTTGGATGGGTATCCGTTTCGGTC
GTCGTGGCGGTCTGCTTATTAGTGCAGTCTGCTTCATCATTTCTGGATTT
GGTGCCGCTACAACGGGATTGACTGGTGATATTGGCTCAGCATTGCCAAT
TTTTTGCTTTTTCCGCTTTTTAGGTGGTTTTGGTATCGGCATCGTTTCGA
CGTTGACTCCAACCTATATTGCTGAAATTGCGCCTCCTGATAAGCGTGGT
CAAATGGTATCTGGTCAACAGATGGCCATCGTAACCGGCGCTTTAACGGG
TTATATCTTCACATGGCTTCTGGCCCATTTTGGTTCTGTTGACTGGATCA
ATGCTAATGGTTGGCGTTGGTCACCTGCATCTGAAGGTATAATTGCTGTT
GTCTTCTTACTGTTACTGTTAACGGCTCCTGATACACCGCATTGGTTGGT
CATGAAGGGCCGCCATTCAGAAGCAAGTAAGATTCTGGCTCGCTTGGAAC
CGCAGGTTGATCCTAGTTTAACGATTCAGAAAATTAAAGCTGGCTTTGAT
AAGGCTTTGCAAAAAAGCAATTCAGGTTTGTTTGCTTTTGGCGCAACCGT

AATCTTCGCTGGTGTTTCAGTCGCTATGTTCCAGCAACTTGTCGGTATTA
ATGCTGTGCTTTACTATGCACCGCAAATGTTCCTGAACTTAGGTTTTGGT
GCTGATACCGCATTACTTCAGACGATTTCAATTGGCGTTGTGAACTTCGT
ATTCACCATGATTGCGTCACGCATTGTTGACCGCTTTGGTCGTAAACCGC
TTCTTATTTGGGGTGGTATCGCGATGGCTGTTATGATGTTTAGCTTAGGT
ATGATGTTCACATATCATATCGGTGGCGTTTTGCCTTTGGCTGCTATTCT
TCTTTACATTGTTGGTTTCGCAATGTCTTGGGGGCCGGTCTGCTGGGTTG
TCCTGTCAGAAATGTTCCCGAATGCTATCAAAGGTTCCGCTATGCCTATT
GCGGTTACCGCGCAATGGATCGCCAATATTTTAGTTAACTTCCTGTTTAA
AATTGCGGATGGTGATCCCGGTTTAAATCGGACTTTCAATCATGGTTTCT
CTTACCTTGTGTTTGCAGGATTAAGTATACTCGGCGCTTTAATCGTCGCA
CGCTTTGTTCCTGAAACGAAAGGACGGAGCCTGGAAGAAATCGAGGAGAT
GTGGCGCTCCTAA

The following sequence is the protein sequence for putative sugar transporter from *Zymomonas mobilis* subspecies *pomaceae* (ATCC 29192).

(SEQ ID NO: 2)
MSSESSQGLVTRLALIAAIGGLLFGYDSAVIAAIGIPVDINFIGPRHLSA
TAAASLSGMVVVAVLAGCVVGSLISGWMGIRFGRRGGLLISAVCFIISGF
GAATTGLTGDIGSALPIFCFFRFLGGFGIGIVSTLTPTYIAEIAPPDKRG
QMVSGQQMAIVTGALTGYIFTWLLAHFGSVDWINANGWRWSPASEGIIAV
VFLLLLLTAPDTPHWLVMKGRHSEASKILARLEPQVDPSLTIQKIKAGFD
KALQKSNSGLFAFGATVIFAGVSVAMFQQLVGINAVLYYAPQMFLNLGFG
ADTALLQTISIGVVNFVFTMIASRIVDRFGRKPLLIWGGIAMAVMMFSLG
MMFTYHIGGVLPLAAILLYIVGFAMSWGPVCWVVLSEMFPNAIKGSAMPI
AVTAQWIANILVNFLFKIADGDPGLNRTFNHGFSYLVFAGLSILGALIVA
RFVPETKGRSLEEIEEMWRS

The following sequences are the polynucleotide encoding xylE and the corresponding polypeptide sequence.

(SEQ ID NO: 4)
ATGAATACCCAGTATAATTCCAGTTATATATTTTCGATTACCTTAGTCGC
TACATTAGGTGGTTTATTATTTGGCTACGACACCGCCGTTATTTCCGGTA
CTGTTGAGTCACTCAATACCGTCTTTGTTGCTCCACAAAACTTAAGTGAA
TCCGCTGCCAACTCCCTGTTAGGGTTTTGCGTGGCCAGCGCTCTGATTGG
TTGCATCATCGGCGGTGCCCTCGGTGGTTATTGCAGTAACCGCTTCGGTC
GTCGTGATTCACTTAAGATTGCTGCTGTCCTGTTTTTTATTTCTGGTGTA
GGTTCTGCCTGGCCAGAACTTGGTTTTACCTCTATAAACCCGGACAACAC
TGTGCCTGTTTATCTGGCAGGTTATGTCCCGGAATTTGTTATTTATCGCA
TTATTGGCGGTATTGGCGTTGGTTTAGCCTCAATGCTCTCGCCAATGTAT
ATTGCGGAACTGGCTCCAGCTCATATTCGCGGGAAACTGGTCTCTTTTAA
CCAGTTTGCGATTATTTTCGGGCAACTTTTAGTTTACTGCGTAAACTATT

-continued
```
TTATTGCCCGTTCCGGTGATGCCAGCTGGCTGAATACTGACGGCTGGCGT
TATATGTTTGCCTCGGAATGTATCCCTGCACTGCTGTTCTTAATGCTGCT
GTATACCGTGCCAGAAAGTCCTCGCTGGCTGATGTCGCGCGGCAAGCAAG
AACAGGCGGAAGGTATCCTGCGCAAAATTATGGGCAACACGCTTGCAACT
CAGGCAGTACAGGAAATTAAACACTCCCTGGATCATGGCCGCAAACCGG
TGGTCGTCTGCTGATGTTTGGCGTGGGCGTGATTGTAATCGGCGTAATGC
TCTCCATCTTCCAGCAATTTGTCGGCATCAATGTGGTGCTGTACTACGCG
CCCGGAAGTGTTCAAACGCTGGGGGCCAGCACGGATATCGCGCTGTTGCA
GACCATTATTGTCGGAGTTATCAACCTCACCTTCACCGTTCTGGCAATTA
TGACGGTGGATAAATTTGGTCGTAAGCCACTGCAAATTATCGGCGCACTC
GGAATGGCAATCGGTATGTTTAGCCTCGGTACCGCGTTTTACACTCAGGC
ACCGGGTATTGTGGCGCTACTGTCGATGCTGTTCTATGTTGCCGCCTTTG
CCATGTCCTGGGGTCCGGTATGCTGGGTACTGCTGTCGGAAATCTTCCCG
AATGCTATTCGTGGTAAAGCGCTGGCAATCGCGGTGGCGGCCCAGTGGCT
GGCGAACTACTTCGTCTCCTGGACCTTCCCGATGATGGACAAAAACTCCT
GGCTGGTGGCCCATTTCCACAACGGTTTCTCCTACTGGATTTACGGTTGT
ATGGGCGTTCTGGCAGCACTGTTTATGTGGAAATTTGTCCCGGAAACCAA
AGGTAAAACCCTTGAGGAGCTGGAAGCGCTCTGGGAACCGGAAACGAAGA
AAACACAACAAACTGCTACGCTGTAA
```
(SEQ ID NO: 5)
MNTQYNSSYIFSITLVATLGGLLFGYDTAVISGTVESLNTVFVAPQNLSE
SAANSLLGFCVASALIGCIIGGALGGYCSNRFGRRDSLKIAAVLFFISGV
GSAWPELGFTSINPDNTVPVYLAGYVPEFVIYRIIGGIGVGLASMLSPMY
IAELAPAHIRGKLVSFNQFAIIFGQLLVYCVNYFIARSGDASWLNTDGWR
YMFASECIPALLFLMLLYTVPESPRWLMSRGKQEQAEGILRKIMGNTLAT
QAVQEIKHSLDHGRKTGGRLLMFGVGVIVIGVMLSIFQQFVGINVVLYYA
PEVFKTLGASTDIALLQTIIVGVINLTFTVLAIMTVDKFGRKPLQIIGAL
GMAIGMFSLGTAFYTQAPGIVALLSMLFYVAAFAMSWGPVCWVLLSEIFP
NAIRGKALAIAVAAQWLANYFVSWTFPMMDKNSWLVAHFHNGFSYWIYGC
MGVLAALFMWKFVPETKGKTLEELEALWEPETKKTQQTATL The following sequences are the polynucleotide encoding xylA and the corresponding polypeptide sequence.

(SEQ ID NO: 6)
```
ATGCAAGCCTATTTTGACCAGCTCGATCGCGTTCGTTATGAAGGCTCAAA
ATCCTCAAACCCGTTAGCATTCCGTCACTACAATCCCGACGAACTGGTGT
TGGGTAAGCGTATGGAAGAGCACTTGCGTTTTGCCGCCTGCTACTGGCAC
ACCTTCTGCTGGAACGGGGCGGATATGTTTGGTGTGGGGCGTTTAATCG
TCCGTGGCAGCAGCCTGGTGAGGCACTGGCGTTGGCGAAGCGTAAGCAG
ATGTCGCATTTGAGTTTTTCCACAAGTTACATGTGCCATTTTATTGCTTC
CACGATGTGGATGTTTCCCCTGAGGGCGCGTCGTTAAAAGAGTACATCAA
TAATTTTGCGCAAATGGTTGATGTCCTGGCAGGCAAGCAAGAAGAGAGCG
```
-continued
```
GCGTGAAGCTGCTGTGGGGAACGGCCAACTGCTTTACAAACCCTCGCTAC
GGCGCGGGTGCGGCGACGAACCCAGATCCTGAAGTCTTCAGCTGGGCGGC
AACGCAAGTTGTTACAGCGATGGAAGCAACCCATAAATTGGGCGGTGAAA
ACTATGTCCTGTGGGGCGGTCGTGAAGGTTACGAAACGCTGTTAAATACC
GACTTGCGTCAGGAGCGTGAACAACTGGGCCGCTTTATGCAGATGGTGGT
TGAGCATAAACATAAAATCGGTTTCCAGGGCACGTTGCTTATCGAACCGA
AACCGCAAGAACCGACCAAACATCAATATGATTACGATGCCGCGACGGTC
TATGGCTTCCTGAAACAGTTTGGTCTGGAAAAAGAGATTAAACTGAACAT
TGAAGCTAACCACGCGACGCTGGCAGGTCACTCTTTCCATCATGAAATAG
CCACCGCCATTGCGCTTGGCCTGTTCGGTTCTGTCGACGCCAACCGTGGC
GATGCGCAACTGGGCTGGGACACCGACCAGTTCCCGAACAGTGTGGAAGA
GAATGCGCTGGTGATGTATGAAATTCTCAAAGCAGGCGGTTTCACCACCG
GTGGTCTGAACTTCGATGCCAAAGTACGTCGTCAAAGTACTGATAAATAT
GATCTGTTTTACGGTCATATCGGCGCGATGGATACGATGGCACTGGCGCT
GAAAATTGCAGCGCGCATGATTGAAGATGGCGAGCTGGATAAACGCATCG
CGCAGCGTTATTCCGGCTGGAATAGCGAATTGGGCCAGCAAATCCTGAAA
GGCCAAATGTCACTGGCAGATTTAGCCAAATATGCTCAGGAACATCATTT
GTCTCCGGTGCATCAGAGTGGTCGCCAGGAACAACTGGAAAATCTGGTAA
ACCATTATCTGTTCGACAAATAA
```
(SEQ ID NO: 7)
MQAYFDQLDRVRYEGSKSSNPLAFRHYNPDELVLGKRMEEHLRFAACYWH
TFCWNGADMFGVGAFNRPWQQPGEALALAKRKADVAFEFFHKLHVPFYCF
HDVDVSPEGASLKEYINNFAQMVDVLAGKQEESGVKLLWGTANCFTNPRY
GAGAATNPDPEVFSWAATQVVTAMEATHKLGGENYVLWGGREGYETLLNT
DLRQEREQLGRFMQMVVEHKHKIGFQGTLLIEPKPQEPTKHQYDYDAATV
YGFLKQFGLEKEIKLNIEANHATLAGHSFHHEIATAIALGLFGSVDANRG
DAQLGWDTDQFPNSVEENALVMYEILKAGGFTTGGLNFDAKVRRQSTDKY
DLFYGHIGAMDTMALALKIAARMIEDGELDKRIAQRYSGWNSELGQQILK
GQMSLADLAKYAQEHHLSPVHQSGRQEQLENLVNHYLFDK The following sequences are the polynucleotide encoding xylB and the corresponding polypeptide sequence.

(SEQ ID NO: 8)
```
ATGTATATCGGGATAGATCTTGGCACCTCGGGCGTAAAAGTTATTTTGCT
CAACGAGCAGGGTGAGGTGGTTGCTGCGCAAACGGAAAAGCTGACCGTTT
CGCGCCCGCATCCACTCTGGTCGGAACAAGACCCGGAACAGTGGTGGCAG
GCAACTGATCGCGCAATGAAAGCTCTGGGCGATCAGCATTCTCTGCAGGA
CGTTAAAGCATTGGGTATTGCCGGCCAGATGCACGGAGCAACCTTGCTGG
ATGCTCAGCAACGGGTGTTACGCCCTGCCATTTTGTGGAACGACGGGCGC
TGTGCGCAAGAGTGCACTTTGCTGGAAGCGCGAGTTCCGCAATCGCGGGT
GATTACCGGCAACCTGATGATGCCCGGATTTACTGCGCCTAAATTGCTAT
GGGTTCAGCGGCATGAGCCGGAGATATTCCGTCAAATCGACAAAGTATTA
```

-continued
TTACCGAAAGATTACTTGCGTCTGCGTATGACGGGGGAGTTTGCCAGCGA

TATGTCTGACGCAGCTGGCACCATGTGGCTGGATGTCGCAAAGCGTGACT

GGAGTGACGTCATGCTGCAGGCTTGCGACTTATCTCGTGACCAGATGCCC

GCATTATACGAAGGCAGCGAAATTACTGGTGCTTTGTTACCTGAAGTTGC

GAAAGCGTGGGTATGGCGACGGTGCCAGTTGTCGCAGGCGGTGGCGACA

ATGCAGCTGGTGCAGTTGGTGTGGGAATGGTTGATGCTAATCAGGCAATG

TTATCGCTGGGGACGTCGGGGGTCTATTTTGCTGTCAGCGAAGGGTTCTT

AAGCAAGCCAGAAAGCGCCGTACATAGCTTTTGCCATGCGCTACCGCAAC

GTTGGCATTTAATGTCTGTGATGCTGAGTGCAGCGTCGTGTCTGGATTGG

GCCGCGAAATTAACCGGCCTGAGCAATGTCCCAGCTTTAATCGCTGCAGC

TCAACAGGCTGATGAAAGTGCCGAGCCAGTTTGGTTTCTGCCTTATCTTT

CCGGCGAGCGTACGCCACACAATAATCCCCAGGCGAAGGGGGTTTTCTTT

GGTTTGACTCATCAACATGGCCCCAATGAACTGGCGCGAGCAGTGCTGGA

AGGCGTGGGTTATGCGCTGGCAGATGGCATGGATGTCGTGCATGCCTGCG

GTATTAAACCGCAAAGTGTTACGTTGATTGGGGGCGGGCGCGTAGTGAG

TACTGGCGTCAGATGCTGGCGGATATCAGCGGTCAGCAGCTCGATTACCG

TACGGGGGGGATGTGGGGCCAGCACTGGGCGCAGCAAGGCTGGCGCAGA

TCGCGGCGAATCCAGAGAAATCGCTCATTGAATTGTTGCCGCAACTACCG

TTAGAACAGTCGCATCTACCAGATGCGCAGCGTTATGCCGCTTATCAGCC

ACGACGAGAAACGTTCCGTCGCCTCTATCAGCAACTTCTGCCATTAATGG

CGTAA (SEQ ID NO: 9)
MYIGIDLGTSGVKVILLNEQGEVVAAQTEKLTVSRPHPLWSEQDPEQWWQ

ATDRAMKALGDQHSLQDVKALGIAGQMHGATLLDAQQRVLRPAILWNDGR

CAQECTLLEARVPQSRVITGNLMMPGFTAPKLLWVQRHEPEIFRQIDKVL

LPKDYLRLRMTGEFASDMSDAAGTMWLDVAKRDWSDVMLQACDLSRDQMP

ALYEGSEITGALLPEVAKAWGMATVPVVAGGGDNAAGAVGVGMVDANQAM

LSLGTSGVYFAVSEGFLSKPESAVHSFCHALPQRWHLMSVMLSAASCLDW

AAKLTGLSNVPALIAAAQQADESAEPVWFLPYLSGERTPHNNPQAKGVFF

GLTHQHGPNELARAVLEGVGYALADGMDVVHACGIKPQSVTLIGGGARSE

YWRQMLADISGQQLDYRTGGDVGPALGAARLAQIAANPEKSLIELLPQLP

LEQSHLPDAQRYAAYQPRRETFRRLYQQLLPLMA

The following sequences are the polynucleotide encoding E. coli glucokinase (glk) and the corresponding polypeptide sequence.

(SEQ ID NO: 10)
ATGACAAAGTATGCATTAGTCGGTGATGTGGGCGGCACCAACGCACGTCT

TGCTCTGTGTGATATTGCCAGTGGTGAAATCTCGCAGGCTAAGACCTATT

CAGGGCTTGATTACCCCAGCCTCGAAGCGGTCATTCGCGTTTATCTTGAA

GAACATAAGGTCGAGGTGAAAGACGGCTGTATTGCCATCGCTTGCCCAAT

TACCGGTGACTGGGTGGCGATGACCAACCATACCTGGGCGTTCTCAATTG

CCGAAATGAAAAAGAATCTCGGTTTTAGCCATCTGGAAATTATTAACGAT

-continued
TTTACCGCTGTATCGATGGCGATCCCGATGCTGAAAAAAGAGCATCTGAT

TCAGTTTGGTGGCGCAGAACCGGTCGAAGGTAAGCCTATTGCGGTTTACG

GTGCCGGAACGGGGCTTGGGGTTGCGCATCTGGTCCATGTCGATAAGCGT

TGGGTAAGCTTGCCAGGCGAAGGCGGTCACGTTGATTTTGCGCCGAATAG

TGAAGAAGAGGCCATTATCCTCGAAATATTGCGTGCGGAAATTGGTCATG

TTTCGGCGGAGCGCGTGCTTTCTGGCCCTGGGCTGGTGAATTTGTATCGC

GCAATTGTGAAAGCTGACAACCGCCTGCCAGAAAATCTCAAGCCAAAAGA

TATTACCGAACGCGCGCTGGCTGACAGCTGCACCGATTGCCGCCGCGCAT

TGTCGCTGTTTTGCGTCATTATGGGCCGTTTTGGCGGCAATCTGGCGCTC

AATCTCGGGACATTTGGCGGCGTGTTTATTGCGGGCGGTATCGTGCCGCG

CTTCCTTGAGTTCTTCAAAGCCTCCGGTTTCCGTGCCGCATTTGAAGATA

AAGGGCGCTTTAAAGAATATGTCCATGATATTCCGGTGTATCTCATCGTC

CATGACAATCCGGGCCTTCTCGGTTCCGGTGCACATTTACGCCAGACCTT

AGGTCACATTCTGTAA (SEQ ID NO: 11)
MTKYALVGDVGGTNARLALCDIASGEISQAKTYSGLDYPSLEAVIRVYLE

EHKVEVKDGCIAIACPITGDWVAMTNHTWAFSIAEMKKNLGFSHLEIIND

FTAVSMAIPMLKKEHLIQFGGAEPVEGKPIAVYGAGTGLGVAHLVHVDKR

WVSLPGEGGHVDFAPNSEEEAIILEILRAEIGHVSAERVLSGPGLVNLYR

AIVKADNRLPENLKPKDITERALADSCTDCRRALSLFCVIMGRFGGNLAL

NLGTFGGVFIAGGIVPRFLEFFKASGFRAAFEDKGRFKEYVHDIPVYLIV

HDNPGLLGSGAHLRQTLGHIL

Example 1

Construction of pCK-pro4-galP-rbsHI-glk

To constitutively express proteins in *E. coli*, pCK-pro4, a low copy number vector carrying a synthetic promoter based on a 670 promoter sequence was used. The plasmid pCK-pro4-galP-rbsHI-glk was constructed in several steps as described below.

Plasmid pCK110900-I-Bla (described in U.S. Pat. No. 7,790,432, herein incorporated by reference, in its entirety) was digested with restriction enzymes XbaI and StuI (Fermentas) following manufacturer recommendations and a synthetic linker containing a σ70 promoter sequence was ligated into this vector in front of the beta-lactamase (Bla) gene. The linker was created by mixing oligos s70-4_F and s70-4_R in equimolar concentrations in 1× PHUSION® DNA polymerase HF-buffer (NEB), heating to 95° C. and cooling the mixture to 10° C. over an hour.

s70-4_F:
(SEQ ID NO: 12)
5'-CCTTTTACGGCTAGCTCAGCCCTAGGTATTATGCTAGCGCT-3' s70-4_R:
(SEQ ID NO: 13)
5'-CTAGAGCGCTAGCATAATACCTAGGGCTGAGCTAGCCGTAAAAGG-3'

The plasmid fragment and linker were ligated using Quick T4 DNA Ligase (NEB) and the reaction was transformed into *E. coli* Top10 electrocompetent cells (Invitrogen) following the manufacturer's protocols. Cells were plated on LB agar plates containing 30 micrograms/ml of chloramphenicol and were incubated overnight at 37° C., as known in the art. Obtained clones were sequence verified and the resulting plasmid was called "pCK-pro4."

The *E. coli* galactose permease (galP) gene was PCR amplified from genomic DNA isolated from strain W3110 using primers NdeI-galP_F and HindIII-PmeI-XhoI-SalI-galP_R, and the product was ligated into the plasmid pCK-pro4. The primer sequences used were:

```
NdeI-galP_F:
                                     (SEQ ID NO: 14)
5'-AAAACATATGCCTGACGCTAAAAAACAGG-3'

HindIII-PmeI-XhoI-SalI-galP_R:
                                     (SEQ ID NO: 15)
5'-AAAAAAGCTTGTTTAAACTTTTCTC
GAGTTTTGTCGACTTAATCGTGAGCGCCTATTTCG-3'
```

The PCR reaction was carried out using the enzyme PHUSION® DNA polymerase (NEB) with an initial denaturation step at 98° C. for 30 sec, followed by 30 cycles of the steps: 98° C. for 5 sec; 63° C. for 20 sec and 72° C. for 40 sec. This was followed by a final elongation step at 72° C. for 5 min. After the PCR reaction, the PCR product was purified through a PCR purification column and eluted with water.

The PCR amplified galP gene and the vector pCK-pro4 were digested with the restriction enzymes NdeI and HindIII (Fermentas) and the resulting products were ligated using Quick T4 DNA ligase (NEB). The reaction product was transformed into *E. coli* electrocompetent cells, following the manufacturer's protocols. Cells were plated on LB agar plates containing 30 ug/ml chloramphenicol, and incubated overnight at 37° C. Chloramphenicol-resistant clones were selected, and plasmid sequences were verified.

The *E. coli* glucokinase (glk) gene was PCR amplified from genomic DNA isolated from strain W3110 using primers SalI-RBS-glk_F and PmeI-glk_R, and the product was ligated into the plasmid pCK-pro4-galP. The primer sequences used were:

```
SalI-RBS-glk_F:
                                     (SEQ ID NO: 16)
5'-AAAAGTCGACAAGGAGGAATAAACCATGACAAAG
TATGCATTAGTCGGT-3'

PmeI-glk_R:
                                     (SEQ ID NO: 17)
5'-AAAAGTTTAAACTTACAGAATGTGACCTAAGGTCTG-3'
```

The PCR reaction was carried out as described above. The PCR-amplified glk gene and the vector pCK-pro4-GalP were digested with the restriction enzymes SalI and PmeI (Fermentas) and the resulting products were ligated using Quick T4 DNA ligase (NEB), following the manufacturer's recommendations. The reaction was transformed into *E. coli* Top10 electrocompetent cells (Invitrogen), following the manufacturer's protocol. Cells were plated on LB agar plates containing 30 ug/ml chloramphenicol and incubated overnight at 37° C. Chloramphenicol-resistant clones were selected, and plasmid sequences were verified.

Example 2

Construction of pCK-pG-Pom-glk

The plasmid pCK-pG-Pom-glk was constructed as described below. The putative glucose facilitator gene from *Zymomonas mobilis* subsp. *pomaceae* (ATCC 29192), termed "Pom", was synthesized and cloned in pUC57 by GenScript. The synthesized gene was based on the native *Z. m. pomaceae* DNA sequence except for the removal of several restriction enzyme sites. This gene was PCR amplified from plasmid pUC57-Pom using primers NdeI-Pom_F and SalI-Pom_R. The primer sequences used were:

```
NdeI-Pom_F:
                                     (SEQ ID NO: 18)
5'-AAAACATATGAGTTCAGAAAGTAGTCAAGGTCT-3'

SalI-Pom_R:
                                     (SEQ ID NO: 19)
5'-AAAAGTCGACTTAGGAGCGCCACATCTCC-3'
```

The PCR reaction was carried out using the enzyme PHUSION® DNA polymerase (NEB), with an initial denaturation step at 98° C. for 30 sec, followed by 30 cycles of the steps: 98° C. for 5 sec; 63° C. for 20 sec and 72° C. for 40 sec. This was followed by a final elongation step at 72° C. for 5 min. The resulting PCR product was purified through a PCR purification column and eluted with water.

The PCR amplified Pom gene and the vector pCK-pro4-GalP-rbsHI-Glk were digested with the restriction enzymes NdeI and SalI (Fermentas) and the resulting products were ligated using Quick T4 DNA ligase (NEB), following manufacturer's recommendations. The reaction product was transformed into *E. coli* Top10 electrocompetent cells (Invitrogen), following the manufacturer's protocols. Cells were plated on LB agar plates containing 30 ug/ml chloramphenicol and incubated overnight at 37° C. Chloramphenicol-resistant clones were selected and verified, to confirm the sequence of pCK-pG-Pom-glk.

Example 3

Construction of pSIM-CDX

The chloramphenicol resistance marker in the lambda-RED expression plasmid pSIM5 (See, Datta et al., Gene 379:109-115 [2006]) was replaced with an ampicillin resistance marker to make plasmid pSIM-CDX as described below.

The ampicillin resistance marker from pUC19 (Invitrogen) was PCR amplified with the following oligos:

```
BLA-Promoter-pSIM5-Mega_F:
                                     (SEQ ID NO: 20)
5'-
GGCAAGGTGTTCTGGTCGGCGCATAGCTGAGA
TAAATGCTTCAATAATATTGAAAAAGGAAGAG-3'

BLA-Promoter-pSIM5-Mega_R:
                                     (SEQ ID NO: 21)
5'-
AGGCAAAGAAAACCCGGCGCTGAGGCCGGGT
TACCAATGCTTAATCAGTGAGGCACCTA-3'
```

The PCR reaction was carried out using the enzyme HERCULASE® DNA polymerase (Agilent) with an initial denaturation step at 94° C. for 2 min., followed by 25 cycles of the steps: 94° C. for 30 sec; 56° C. for 30 sec and 72° C. for 2 min. This was followed by a final elongation step at 72° C. for 3 min. The resulting PCR product was cleaned with ExoSAP-IT (Affymetrix) and the remaining template was digested with DpnI (Promega). Five microliters of cleaned PCR product was added to 40 ng of plasmid pSIM5. This mixture was PCR amplified using PHUSION® DNA polymerase (NEB), with an initial denaturation step at 98° C. for 30 sec, followed by 40 cycles of the steps: 98° C. for 10 sec; 72 for 3 min. This was followed by a final elongation step at 72° C. for 5 min. After the PCR reaction, the product was digested with DpnI (Promega). This reaction product was transformed into *E. coli* DH10B electrocompetent cells (Invitrogen), following the manufacturer's protocols. Cells were plated on LB agar plates containing 50 ug/ml carbenicillin and incubated 24 hours, at 30° C. Carbenicillin-resistant clones were obtained and plasmid sequences verified.

Example 4

Generating *E. coli* Strain W3110K-ΔptsHI-crr::Km

The ptsHI-crr operon was deleted from *E. coli* strain W3110K (*E. coli* Genetic Stock Center (CGSC) strain #7167), using the known technique of lambda RED-mediated homologous recombination as described below. A dsDNA kanamycin resistance cassette was PCR amplified from plasmid pKD13 (See, Datsenko and Wanner, Proc. Natl. Acad. Sci. USA 97:6640-5 [2000]) using the following primers:

```
ptsHI-crr-(dsDNA-2,18)_F:
                                    (SEQ ID NO: 22)
5'-CCACAACACTAAACCTATAAGTTGGGGAAATA
CAATGTTCATTCCGGGG ATCCGTCGACC-3' ptsHI-crr-(dsDNA-2,18)_R:
                                    (SEQ ID NO: 23)
5'-TAACCGGGGTTTCACCCACGGTTACGCTACC
GGACAGTTTTGTAGG CTGGAGCTGCTTCG-3'
```

The PCR reaction was carried out using PHUSION® DNA polymerase (NEB), with an initial denaturation step at 98° C. for 30 sec, followed by 30 cycles of the steps: 98° C. for 5 sec; 63° C. for 20 sec and 72° C. for 40 sec. This was followed by a final elongation step at 72° C. for 5 min. After the PCR reaction, the PCR product was purified through a PCR purification column and eluted with water, using methods known in the art.

Strain W3110K was transformed with plasmid pSIM5, to generate lambda-RED recombination proficient electrocompetent cells as described by Datta et al. (Datta et al., Gene 379:109-115 [2006]). Briefly, cells grown to log-phase at 32° C. were induced at 42° C. for 15 minutes and electrocompetent cells were prepared by washing twice with ice cold water. Competent cells were transformed with 500 ng of the kanamycin cassette from above. Cells were recovered at 32° C. for three hours, plated on LB agar plates containing 20 micrograms/ml of kanamycin, and incubated overnight at 37° C. A colony confirmed to have the ptsHI-crr operon replaced with the kanamycin cassette was purified and used for subsequent experiments. This strain was named "W3110K-ΔptsHI-crr::Km."

Example 5

Generating *E. coli* Strain W3110K-ΔptsHI-crr::Km—insH11::pG-Pom-glk

The *E. coli* strain W3110K-ΔptsHI-crr::Km—insH11::pG-Pom-glk was constructed using lambda RED-mediated homologous recombination as described below. A dsDNA cassette was PCR amplified from plasmid pCK-pG-Pom-glk using the following oligos:

```
pA3-insert(insH11)_F:
                                    (SEQ ID NO: 24)
5'-
TCTTTCATACAATGACATATTAAAATATCAGCAAGAATTCCAAAGGGTGA
AACAAAACGGTTNACAACATGAAGTAAACACGGTACGNTGTACCACATGA
AACGACAGTGAGTCAAGCCTGGCCATAAGGAGATATACAT-3' pCK-chlor(insH11)_R:
                                    (SEQ ID NO: 25)
5'-
TTGAAATACTTCGAATTGATATTCAGACATTTCTGCCCATGTTTGCTGAA
AGGACAAGTTTTGGTGACTG-3'
```

The resulting cassette encoded the putative glucose facilitator gene from *Z. mobilis* subsp. *pomaceae* (ATCC 29192) and the *E. coli* glucokinase (glk) gene expressed from a constitutive promoter "library" with single degenerate nucleotides at the −10 and −25 positions. In addition, the cassette contained a chloramphenicol resistance marker expressed from a separate, constitutive promoter.

The PCR reaction was carried out using HERCULASE® II fusion DNA polymerase (Agilent) with an initial denaturation step at 95° C. for 2 min., followed by 30 cycles of the steps: 95° C. for 20 sec; 63° C. for 20 sec and 72° C. for 3 min. This was followed by a final elongation step at 72° C. for 3 min. After the PCR reaction, the PCR product was purified through a PCR purification column and eluted with water.

Strain W3110K-ΔptsHI-crr::Km (Example 4) was transformed with the plasmid pSIM-CDX (Example 3) and recombination proficient electrocompetent cells were generated as described by Datta et al., supra. Competent cells were transformed with 500 ng of the cassette from above and were recovered at 32° C. for five hours. Recovered cells were plated on M9 minimal media agar (Difco™ M9 Minimal Salts, Cat. No. 248510) supplemented with MgSO$_4$, CaCl$_2$, 0.5% glucose, and 15 micrograms/ml of chloramphenicol. After several days of growth at 30° C., a large colony (capable of growing well on the M9-glucose minimal media plates) was purified and the integration of the cassette was verified. This cloned strain was named "W3110K-ΔptsHI-crr::Km—insH11::pG-Pom-glk."

Example 6

Construction of pCK-pro4-xylE

The plasmid pCK-pro4-xylE was constructed as described below. The *E. coli* D-xylose-proton symporter (xylE) gene was PCR-amplified from genomic DNA isolated from strain W3110 using primers NdeI-xylE_F and HindIII-PmeI-XhoI-SalI-xylE_R, and the product was ligated into the plasmid pCK-pro4. The primer sequences are provided below:

```
NdeI-xylE_F:
                                    (SEQ ID NO: 26)
5'-AAAACATATGAATACCCAGTATAATTCCAGTTATATATTTTC-3'

HindIII-PmeI-XhoI-SalI-xylE_R:
                                    (SEQ ID NO: 27)
5'-AAAAAAGCTTGTTTAAACTTTTCTCGAGTTACAGCGTAGCA
GTTTGTTGT-3'
```

The PCR reaction was carried out using PHUSION® DNA polymerase (NEB), with an initial denaturation step at 98° C. for 30 sec, followed by 30 cycles of the steps: 98° C. for 5 sec; 63° C. for 20 sec and 72° C. for 40 sec. This was followed by a final elongation step at 72° C. for 5 min. After the PCR reaction, the PCR product was purified through a PCR purification column and eluted with water, as known in the art.

The PCR amplified xylE gene and the vector pCK-pro4 were digested with NdeI and HindIII (Fermentas) and the resulting products were ligated using Quick T4 DNA ligase (NEB), following the manufacturer's recommendations. The reaction product was transformed into *E. coli* Top10 electrocompetent cells (Invitrogen), following the manufacturer's protocols. Cells were plated on LB agar plates containing 30 micrograms/ml of chloramphenicol and were incubated overnight at 37° C. Obtained clones were sequence verified.

Example 7

Generating *E. coli* Strain W3110K—ΔptsHI-crr:: Km—ΔxylFGH::pAB-pE-xylE

The *E. coli* strain W3110K-ΔptsHI-crr::Km—ΔxylFGH:: pAB-pE-xylE was constructed in several steps as described below:

(a) A dsDNA cassette was PCR amplified from the plasmid pCK-pro4-xylE (Example 6) using the following oligos:

```
Consensus-insert(xylFGH)_F:
                                  (SEQ ID NO: 28)
5'-
AAGAGAAAAATGCAATAAGTACAATTGCGCAACAAAAGTAAGATCGGTTT
TTTTAGGCCTTTNACAGCTAGCTCAGTCCTAGGTATNNTGCTAGCATACT
AGAGGCCAGCCTGGCCATAAGGAGATATACAT-3' pCK-chlor(xylFGH)_R:
                                  (SEQ ID NO: 29)
5'-
TCAAGAACGGCGTTTGGTTGCGGAGTCCATCCATACTGCCAGCAACTGAA
AGGACAAGTTTTGGTGACTG-3'
```

The resulting cassette encoded the *E. coli* xylose-proton symporter (xylE) expressed from a synthetic constitutive promoter "library" with degenerate nucleotides at the −10 and −35 positions. The PCR reaction was carried out using HERCULASE® II fusion DNA polymerase (Agilent) with an initial denaturation step at 95° C. for 2 min., followed by 30 cycles of the steps: 95° C. for 20 sec; 63° C. for 20 sec and 72° C. for 3 min. This was followed by a final elongation step at 72° C. for 3 min. After the PCR reaction, the PCR product was purified through a PCR purification column and eluted with water, as known in the art.

(b) A second dsDNA cassette was PCR amplified from the cassette described in part (a) using the following oligos:

```
xylAB-pro-mod_F:
                                  (SEQ ID NO: 30)
5'-
GAACTCCATAATCAGGTAATGCCGCGGGTGATGGATGATGTCGTAANNAT
AGGCACTCCCTTTAAATATGTNAAGAATTATTTTTATAGAACGCAGCTGC
GGGCTGTTACCGCGTTCGGGTGCGATAAAAAGTAAGATCGGTTTTTTTAG
GCCTTT-3' pCK-chlor(xylFGH)_R:
                                  (SEQ ID NO: 31)
5'-
TCAAGAACGGCGTTTGGTTGCGGAGTCCATCCATACTGCCAGCAACTGAA
AGGACAAGTTTTGGTGACTG-3'
```

The second PCR product contained regions of homology to the genome designed such that the cassette replaced the native xylFGH operon with the xylE gene expressed from a synthetic constitutive promoter "library" and replaced the native xylAB promoter with a second synthetic constitutive promoter "library." In addition, the cassette contained a chloramphenicol resistance marker expressed from a separate, constitutive promoter. The PCR reaction was carried out using HERCULASE® II fusion DNA polymerase (Agilent), with an initial denaturation step at 95° C. for 2 min., followed by 30 cycles of the steps: 95° C. for 20 sec; 63° C. for 20 sec and 72° C. for 3 min. This was followed by a final elongation step at 72° C. for 3 min. After the PCR reaction, the PCR product was purified through a PCR purification column and eluted with water.

(c) Strain W3110K-ΔptsHI-crr::Km (Example 4) was transformed with the plasmid pSIM-CDX (Example 3) and recombination proficient electrocompetent cells were prepared as described by Datta et al., supra. Competent cells were transformed with 500 ng of the cassette from above and were recovered at 32° C. for five hours. Recovered cells were plated on M9 minimal media agar (Difco™ M9 Minimal Salts, Cat. No. 248510) supplemented with MgSO$_4$, CaCl$_2$, 0.5% xylose, and 15 micrograms/ml of chloramphenicol. After several days of growth at 30° C., a large colony (capable of growing well on the M9-xylose minimal media plates) was purified and the integration of the cassette was verified. This cloned strain was named "W3110K-ΔptsHI-crr::Km—ΔxylFGH::pAB-pE-xylE."

Example 8

Generating *E. coli* Strain W3110K-ΔptsHI-crr:: Km—insH11::pG-Pom-glk—ΔxylFGH::pAB-pE-xylE The *E. coli* strain W3110K-ΔptsHI-crr::Km—insH11:: pG-Pom-glk—ΔxylFGH::pAB-pE-xylE was constructed as described below. The ΔxylFGH::pAB-pE-xylE cassette was PCR amplified from strain W3110K-ΔptsHI-crr::Km-ΔxylFGH::pAB-pE-xylE (Example 7) using the following oligos:

```
xylFGH-check_F:
                                  (SEQ ID NO: 32)
5'-CCGATTGTGACGCCTGTAAA-3' xylFGH-check_R:
                                  (SEQ ID NO: 33)
5'-CGCAAGTGCTCTTCCATACG-3'
```

The PCR reaction was carried out using the enzyme HERCULASE® II fusion DNA polymerase (Agilent) with an initial denaturation step at 95° C. for 2 min., followed by 30 cycles of the steps: 95° C. for 20 sec; 55° C. for 20 sec and 72° C. for 3 min. This was followed by a final elongation step at 72° C. for 3 min. After the PCR reaction, the PCR product was purified through a PCR purification column and eluted with water, as known in the art.

Strain W3110K-ΔptsHI-crr::Km—insH11::pG-Pom-glk (Example 5) was transformed with the plasmid pSIM-CDX (Example 3) and electro competent cells were prepared as described by Datta et al., supra. Competent cells were transformed with 500 ng of the cassette from above and were recovered at 32° C. for five hours. Recovered cells were plated on M9 minimal media agar (Difco™ M9 Minimal Salts, Cat. No. 248510) supplemented with MgSO$_4$, CaCl$_2$, 0.5% xylose. After several days of growth at 30° C., a large colony (capable of growing well on the M9-xylose minimal media plates) was purified and the integration of the cassette was verified. This cloned strain was named "W311 OK-ΔptsHI-crr::Km—insH11::pG-Pom-glk—ΔxylFGH::pAB-pE-xylE."

Example 9

Generating E. coli Strain W3110K-ΔxylFGH::pAB-pE-xylE

The *E. coli* strain W3110K-ΔxylFGH::pAB-pE-xylE was constructed in several steps as described below:

(a) A dsDNA cassette was PCR amplified from the plasmid pCK-pro4-xylE (Example 6) using the following oligos:

```
Consensus-insert(xylFGH)_F:
                                      (SEQ ID NO: 34)
5'-
AAGAGAAAAATGCAATAAGTACAATTGCGCAACAAAAGTAAGATCGGTTT
TTTTAGGCCTTTNACAGCTAGCTCAGTCCTAGGTATNNTGCTAGCATACT
AGAGGCCAGCCTGGCCATAAGGAGATATACAT-3' pCK-chlor(xylFGH)_R:
                                      (SEQ ID NO: 35)
5'-
TCAAGAACGGCGTTTGGTTGCGGAGTCCATCCATACTGCCAGCAACTGAA
AGGACAAGTTTTGGTGACTG-3'
```

The resulting cassette encoded the *E. coli* xylose-proton symporter (xylE) expressed from a constitutive promoter "library" with degenerate nucleotides at the −10 and −35 positions. The PCR reaction was carried out using HERCULASE® II fusion DNA polymerase (Agilent), with an initial denaturation step at 95° C. for 2 min., followed by 30 cycles of the steps: 95° C. for 20 sec; 63° C. for 20 sec and 72° C. for 3 min. This was followed by a final elongation step at 72° C. for 3 min. After the PCR reaction, the PCR product was purified through a PCR purification column and eluted with water, as known in the art.

(b) A second dsDNA cassette was PCR amplified from the cassette described in part (a) using the following oligos:

```
xylAB-pro-mod_F:
                                      (SEQ ID NO: 36)
5'-
GAACTCCATAATCAGGTAATGCCGCGGGTGATGGATGATGTCGTAANNAT
AGGCACTCCCTTTAAATATGTNAAGAATTATTTTTATAGAACGCAGCTGC
GGGCTGTTACCGCGTTCGGGTGCGATAAAAAGTAAGATCGGTTTTTTAG
GCCTTT-3' pCK-chlor(xylFGH)_R:
                                      (SEQ ID NO: 37)
5'-
TCAAGAACGGCGTTTGGTTGCGGAGTCCATCCATACTGCCAGCAACTGAA
AGGACAAGTTTTGGTGACTG-3'
```

The second PCR product contained regions of homology to the genome and was designed such that the cassette replaced the native xylFGH operon with the xylE gene expressed from a constitutive promoter "library" and replaced the native xylAB promoter with a second synthetic constitutive promoter "library." In addition, the cassette contained a chloramphenicol resistance marker expressed from a separate, constitutive promoter. The PCR reaction was carried out using HERCULASE® II fusion DNA polymerase (Agilent) with an initial denaturation step at 95° C. for 2 min., followed by 30 cycles of the steps: 95° C. for 20 sec; 63° C. for 20 sec and 72° C. for 3 min. This was followed by a final elongation step at 72° C. for 3 min. After the PCR reaction, the PCR product was purified through a PCR purification column and eluted with water, as known in the art.

(c) Strain W3110K was transformed with the plasmid pSIM-CDX (Example 3) and recombination proficient electrocompetent cells were prepared as described by Datta et al., supra. Competent cells were transformed with 500 ng of the cassette from above and were recovered at 32° C. for five hours. Recovered cells were plated on M9 minimal media agar (Difco™ M9 Minimal Salts, Cat. No. 248510) supplemented with MgSO$_4$, CaCl$_2$, 0.5% xylose, and 15 micrograms/ml of chloramphenicol. After several days of growth at 30° C., a large colony (capable of growing well on the M9-xylose minimal media plates) was purified and the integration of the cassette was verified. This cloned strain was named "W3110K-ΔxylFGH::pAB-pE-xylE."

Example 10

Assay for Growth and Sugar Utilization

To determine cell growth and sugar utilization rates, *E. coli* strains were grown in minimal media supplemented with glucose and/or xylose as described below. Relevant *E. coli* strains were streaked for single colonies on LB agar plates and grown overnight at 37° C. For each strain, a single colony was transferred to 2 ml of LB (Luria-Bertani) media in a 14 mL round-bottom culture tube and grown for approximately 10 hours at 30° C., 250 rpm. Then, 250 uL of each culture was used to inoculate 125 ml baffled Erlenmeyer flasks containing 25 ml of fresh M9 minimal media (Difco™ M9 Minimal Salts, Cat. No. 248510), supplemented with 0.5% glucose, 0.5% xylose, or 0.25% glucose plus 0.25% xylose as appropriate. Flasks were grown for 36 hours at 30° C. and 150 µl samples were taken periodically for analysis.

For each sample, the OD$_{600}$ was measured, and the residual glucose, xylose, and byproducts from growth, such as acetate and lactate, were determined with HPLC analysis as described below. Samples were analyzed with an Agilent 1200 HPLC equipped with a refractive index detector (RID). Glucose, xylose, acetate, lactate, and other metabolites of interest were separated on an ion-exchange column (Aminex HPX-87H; Bio-Rad) at 80° C. The elution was performed isocratically with a mobile phase of 5 mM H$_2$SO$_4$ at a flow rate of 0.6 ml/min. Retention times were determined empirically by comparison to commercial standards (Sigma-Aldrich). For a 20 minute run cycle, approximate run times were as follows: glucose; 9.3 min, xylose; 9.9 min, acetic acid; 14.7 min, and lactic acid; 12.7 min.

Example 11

Figure 2A:
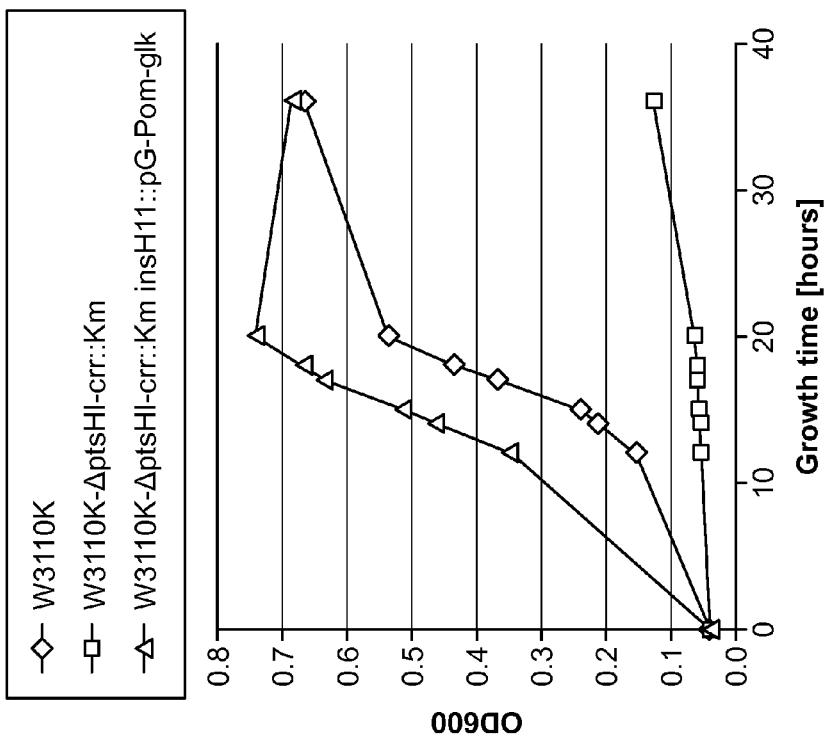
Figure 4A:
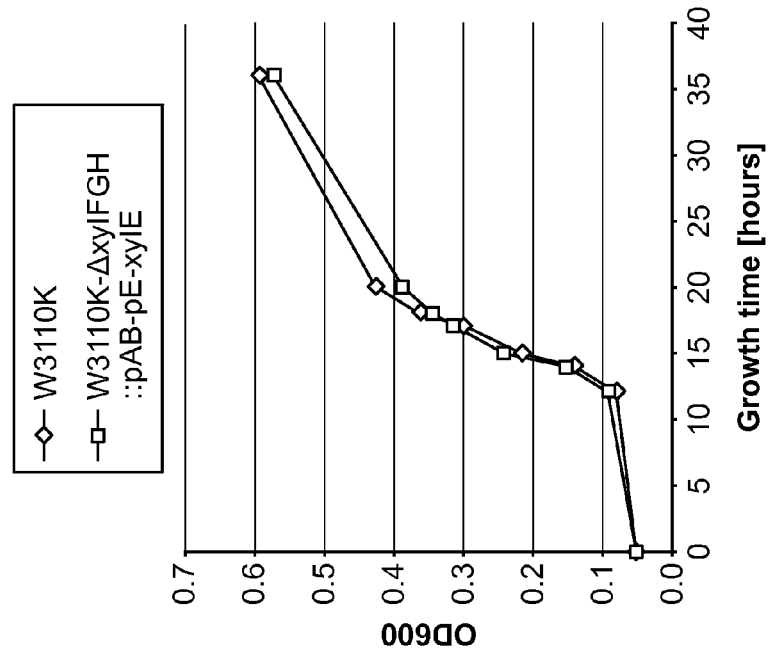
FIG. 4 provides graphs showing cell growth curves for *E. coli* cell lines W3110K (wild-type) and W3110K-ΔxylFGH::pAB-pE-xylE grown in shake flask in M9 minimal media. Panel A provides the growth curves for cells grown in media supplemented with 0.5% glucose; Panel B provides the growth curves for cells grown in media containing 0.5% xylose; and Panel C provides the growth curves for cells grown in media containing 0.25% glucose plus 0.25% xylose. Panel D provides sugar consumption curves for the cells shown in Panel C. Both cell lines had similar growth curves when grown in glucose or xylose only. When grown in glucose plus xylose, W3110K-ΔxylFGH::pAB-pE-xylE demonstrated co-utilization of glucose and xylose compared with the wild-type cells which showed standard diauxic growth.
Figure 4B:
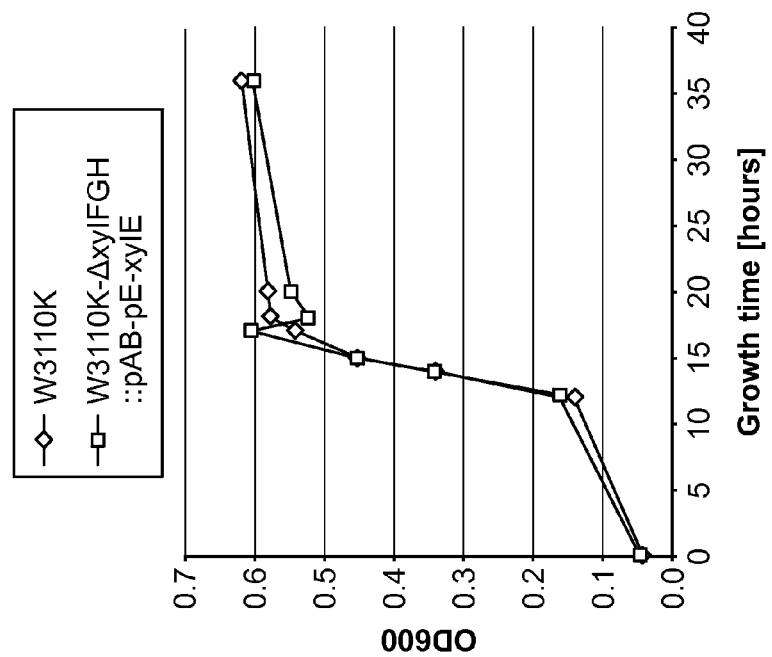
Figure 4D:
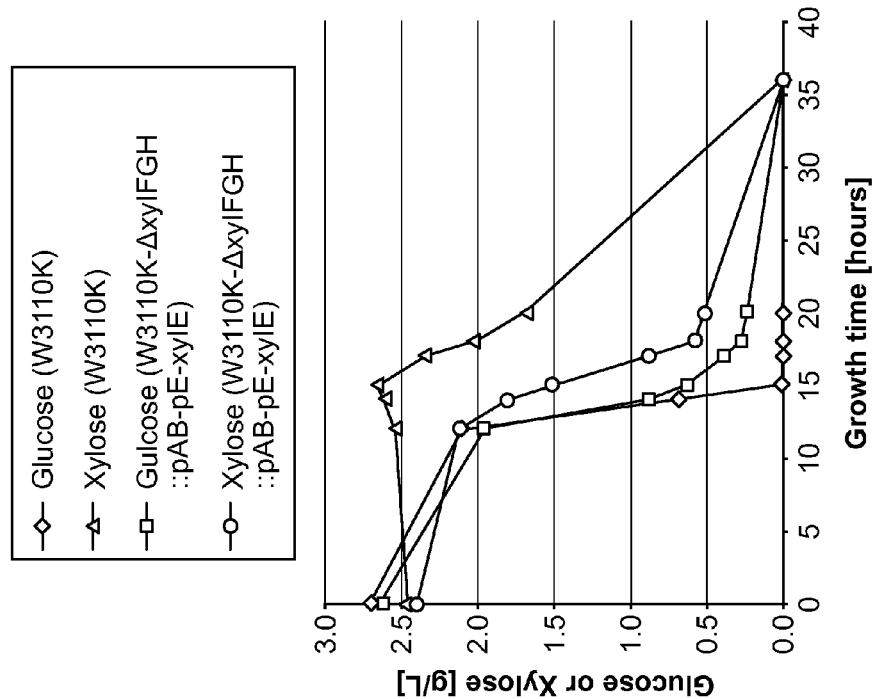
Figure 4C:
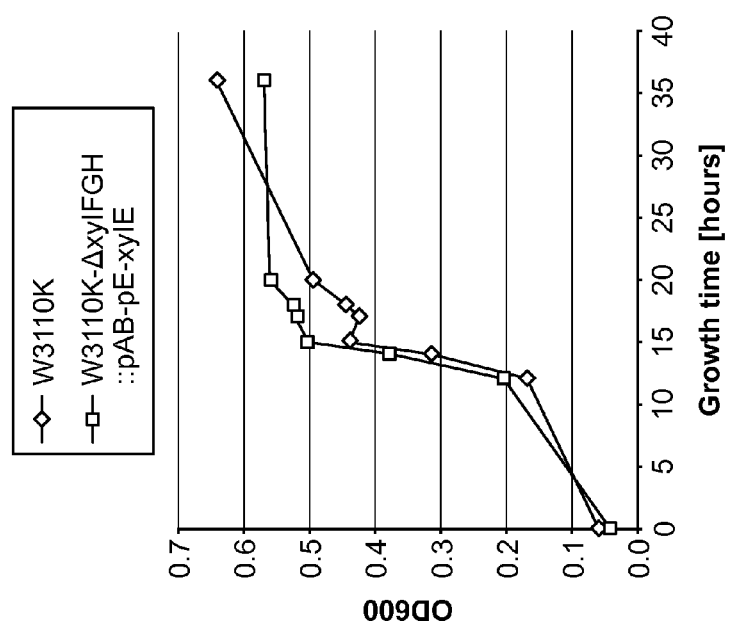

Glucose Utilization in *E. coli* Strain Expressing *Z. mobilis* subsp. *pomaceae* Putative Sugar Transporter Strain W3110K-ΔptsHI-crr::Km—insH11::pG-Pom-glk, a PTS⁻ strain expressing the putative glucose facilitator gene from *Z. mobilis* subsp. *pomaceae* and the *E. coli* glucokinase (glk), was assayed for restoration of glucose utilization. As shown in FIG. 2, strain W3110K-ΔptsHI-crr::Km did not utilize glucose well. Expression of the putative glf gene from *Zymomonas mobilis* subsp. *pomaceae* (ATCC 29192) and the native glk gene in W3110K-ΔptsHI-crr restored glucose utilization and growth on glucose to levels in excess of the W3110K wild-type cells.

Example 12

Glucose and Xylose Co-Utilization in *E. coli* Strain Expressing *Z. mobilis* Subsp. *Pomaceae* Putative Sugar Transporter and *E. coli* Xylose Symporter XylE Fatty alcohol production by W3110K and W3110K-ΔptsHI-crr::Km—insH11::pG-Pom-glk—ΔxylFGH::pAB-pE-xylE cells transformed with a fatty acid reductase (FAR)-expressing plasmid, was measured using 10 L fermentors (Biostat C-Plus, Sartorius) and cellulosic hydrolysate as the primary carbon and energy source, according to the following procedure. The whole fermentation duration was 91 hr, carried out at 30° C. and pH 7.0 with dissolved oxygen above 30% of saturation. The inoculum was prepared in M9 media, 1% glucose and 2 g/L yeast extract containing spectinomycin at 100 micrograms ml$^{-1}$. A determined volume of the inoculum was used to inoculate 3 L of sterile phosphate-limited ("P-lim") medium to a final $OD_{600}$ of 0.05.

The P-lim medium composition was as follows: 6.4 g/L and 3.6 g/L glucose and xylose respectively, from cellulosic hydrolysate; 0.87 g/L ammonium sulfate; 3 g/L potassium phosphate dibasic anhydrous; 0.05 g/L magnesium sulfate; 3.33 g/L yeast extract; 1 g/L sodium citrate dehydrate; 0.33 g/L ammonium iron (III) citrate; 2.1 mg/L cobalt chloride hexahydrate; 12.5 mg/L manganese (II) chloride tetrahydrate; 1.25 mg/L copper (II) chloride dihydrate; 2.5 mg/L boric acid; 2.1 mg/L sodium molybdate dihydrate; 10.8 mg/L zinc acetate dihydrate; 100 mg/L spectinomycin.

After inoculation, the cells were grown in batch mode until the exhaustion of the carbon sources as signified by a dissolved oxygen spike. At this moment, FAR expression was induced with 1 mM IPTG (final concentration) and a second fed-batch phase was started. In this phase, a non-sterile cellulosic hydrolysate containing 207 g/L of glucose and 116 g/L of xylose (the major sugar species) supplemented with 2 g/L $MgSO_4$ was fed in order to maintain a growth rate of 0.15 hr$^{-1}$. At around an $OD_{600}$ of 50, the culture exhausted the initial phosphate source. From this point to the end of the fermentation, phosphate was added continuously at 40 mmol/hr (using a 50 g/L $KH_2PO_4$ solution) and the carbon source (from the cellulosic hydrolysate) was pumped to deliver a continuous feed of 19.2 g/hr and 10.8 g/hr of glucose and xylose, respectively. Samples were taken to evaluate sugars, nitrogen, and phosphate consumption as well as fatty alcohol and by-products production.

As shown in FIG. 3, the modified strain produced an increased amount of fatty alcohol, had improved specific productivity (as measured in grams of FOH per gram of cellulosic sugar per hour), and exhibited increased fatty alcohol yield (as measured in grams of FOH per gram of cellulosic sugar) at various time points as compared to wild-type cells.

Example 13

Figure 5A:
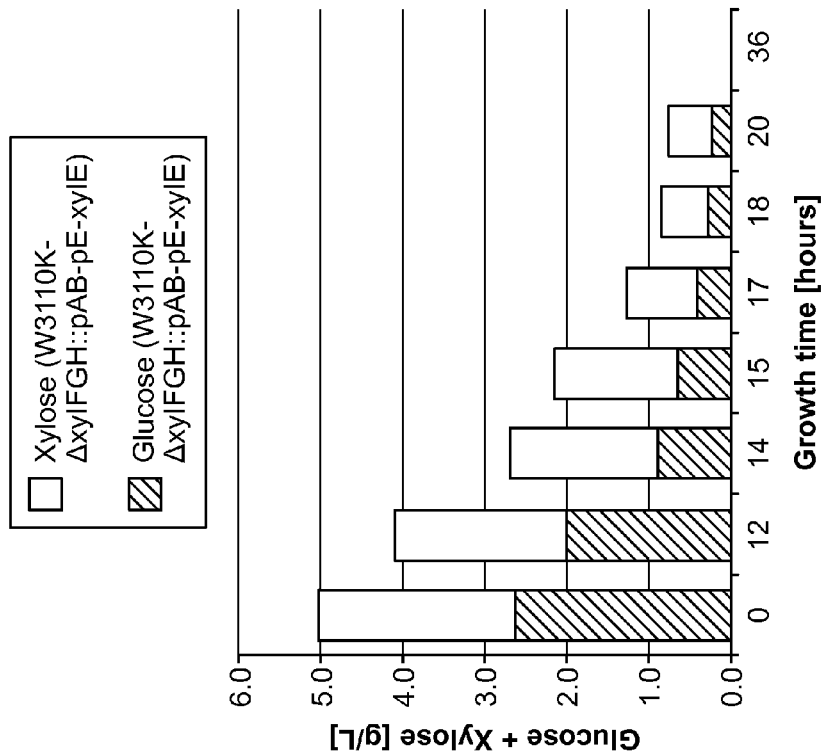
FIG. 5 provides graphs showing total sugar (grams per liter of glucose plus xylose) remaining for *E. coli* cell lines. Panel A provides results for W3110K and Panel B provides results for W3110K-ΔxylFGH::pAB-pE-xylE grown in shake flasks in M9 minimal media supplemented with 0.25% glucose plus 0.25% xylose. W3110K wild-type cells used all glucose before consuming xylose while W3110K-ΔxylFGH::pAB-pE-xylE utilized both sugars simultaneously. At the 18 hour time point, strain W3110K-ΔxylFGH::pAB-pE-xylE had used 32% more sugar than the W3110K wild-type cells (0.85 g/l total sugar remaining versus 2.03 g/l for the W3110K wild-type cells).
Figure 5B:
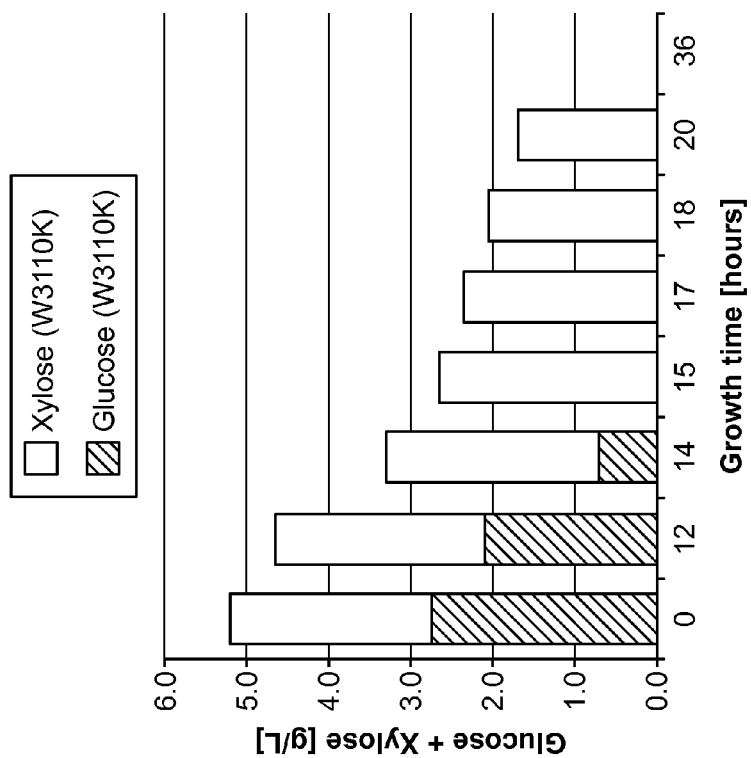

Glucose and Xylose Co-Utilization in *E. coli* Strain Overexpressing *E. coli* Xylose Symporter XylE Strain W3110K-ΔxylFGH::pAB-pE-xylE, a PTS+ strain expressing an *E. coli* D-xylose-proton symporter (xylE) and xylAB under the control of constitutive promoters, was assayed for glucose and xylose co-utilization. Both a wild-type cell line (W3110K) and a clone from the W3110K-ΔxylFGH::pAB-pE-xylE strain were grown in shake flasks with M9 minimal media supplemented with 0.25% glucose and 0.25% xylose. As shown in FIGS. 4 and 5, W3110K wild-type cells used substantially all of the glucose before consuming xylose, while W3110K-ΔxylFGH::pAB-pE-xylE cells utilized both sugars simultaneously. Additionally, cells overexpressing XylE consumed sugars faster than the wild-type cells. Table 1 shows the total sugar (grams per liter of glucose plus xylose) remaining for the cell lines at various time points. At the 18 hour time point, strain W3110K-ΔxylFGH::pAB-pE-xylE had used 32% more sugar than the W3110K wild-type cells (0.85 g/l total sugar remaining versus 2.03 g/l for the W3110K wild-type cells).

TABLE 1

| Total Sugar Consumption for Wild-Type or XylE-Overexpressing Cell Lines | | |
|---|---|---|
| Growth Time (hours) | W3110K | W3110K-xylFGH:: pAB-pE-xylE |
| 0 | 5.19 | 5.03 |
| 12 | 4.65 | 4.09 |
| 14 | 3.31 | 2.70 |
| 15 | 2.66 | 2.15 |
| 17 | 2.35 | 1.27 |
| 18 | 2.03 | 0.85 |
| 20 | 1.69 | 0.76 |
| 36 | 0.00 | 0.00 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for producing an end-product from a biomass substrate comprising glucose and xylose, the method comprising:
   providing an *E. coli* host cell, wherein the host cell has a phosphoenolpyruvate-dependent phosphotransferase transfer system negative (PTS⁻) phenotype and wherein the host cell has been modified to express:
   (i) a first gene encoding a polypeptide having glucose transport activity, wherein the first gene is operably linked to a first heterologous promoter, and wherein the polypeptide having glucose transport activity comprises the amino acid sequence of SEQ ID NO:2; and
   (ii) a second gene encoding a polypeptide having xylose transport activity, wherein the second gene is operably linked to a second heterologous promoter, and wherein said second gene encodes a polypeptide comprising the sequence of SEQ ID NO:5;
   contacting the modified host cell with the biomass substrate; and
   culturing the modified host cell under suitable culture conditions, wherein said end-product is produced.

2. The method of claim 1, further comprising modifying the host cell to express a third gene encoding a glucokinase protein, wherein the third gene is operably linked to a third heterologous promoter.

3. The method of claim 1, wherein one or more of the first promoter, second promoter, or third promoter is a constitutive promoter.

4. The method of claim 1, wherein one or more of the first gene, second gene, or third gene is integrated into the genome of the host cell.

5. The method of claim 1, wherein the host cell is further modified to delete or substantially inactivate an endogenous gene encoding a xylose ABC transporter.

6. The method of claim 1, wherein the PTS⁻ phenotype is caused by deletion or inactivation of all or substantially all of one or more of genes selected from ptsH, ptsI, and crr.

7. The method of claim 1, wherein the end-product is an alcohol, or a hydrocarbon.

* * * * *

SEQUENCE LISTING

```
<160> NUMBER OF SEQ ID NOS: 37

<210> SEQ ID NO 1
<211> LENGTH: 1413
<212> TYPE: DNA
<213> ORGANISM: Zymomonas mobilis

<400> SEQUENCE: 1
atgagttcag aaagtagtca aggtctagtc acgcgactag ccttaattgc cgccattggc      60
ggtctactat ttggttacga ttcagccgtt attgctgcga tcggtataac ggttgatatt     120
```

```
aactttattg gtccccgcca tctgtcagct accgctgccg cctcccttc agggatggtg    180 gttgttgctg tcttggcagg ttgtgttgtt ggttcattaa tttccggttg gatgggtatc    240
cgtttcggtc gtcgtggcgg tctgcttatt agtgcagtct gcttcatcat ttctggattt    300
ggtgccgcta caacgggatt gactggtgat attggctcag cattgccaat ttttgctt     360 ttccgcttt aggtggtttt ggtatcggc atcgtttcga cgttgactcc aacctatatt    420
gctgaaattg cgcctcctga taagcgtggt caaatggtat ctggtcaaca gatgccatc    480 gtaaccggcg ctttaacggg ttatatcttc acatggcttc tggcccattt tggttctgtt    540
gactggatca atgctaatgg ttggcgttgg tcacctgcat ctgaaggtat aattgctgtt    600
gtcttcttac tgttactgtt aacggctcct gatacaccgc attggttggt catgaagggc    660
cgccattcag aagcaagtaa gattctggct cgcttggaac cgcaggttga tcctagttta    720
acgattcaga aaattaaagc tggctttgat aaggctttgc aaaaaagcaa ttcaggtttg    780
tttgcttttg gcgcaaccgt aatcttcgct ggtgtttcag tcgctatgtt ccagcaactt    840
gtcggtatta atgctgtgct ttactatgca ccgcaaatgt tcctgaactt aggttttggt    900
gctgataccg cattacttca gacgatttca attggcgttg tgaacttcgt attcaccatg    960
attgcgtcac gcattgttga ccgctttggt cgtaaaccgc ttcttatttg gggtggtatc    1020
gcgatggctg ttatgatgtt tagcttaggt atgatgttca catatcatat cggtggcgtt    1080 ttgccttgg ctgctattct tctttacatt gttggtttcg caatgtcttg ggggccggtc    1140
tgctgggttg tcctgtcaga atgttcccg aatgctatca aggttccgc tatgcctatt    1200 gcggttaccg cgcaatggat cgccaatatt ttagttaact tcctgtttaa aattgcggat    1260
ggtgatcccg gtttaaatcg gactttcaat catggtttct cttaccttgt gtttgcagga    1320
ttaagtatac tcggcgcttt aatcgtcgca cgctttgttc ctgaaacgaa aggacggagc    1380
ctggaagaaa tcgaggagat gtggcgctcc taa                                 1413
```

<210> SEQ ID NO 2
<211> LENGTH: 470
<212> TYPE: PRT
<213> ORGANISM: Zymomonas mobilis

<400> SEQUENCE: 2

```
Met Ser Ser Glu Ser Ser Gln Gly Leu Val Thr Arg Leu Ala Leu Ile
1               5                   10                  15

Ala Ala Ile Gly Gly Leu Leu Phe Gly Tyr Asp Ser Ala Val Ile Ala
            20                  25                  30

Ala Ile Gly Ile Pro Val Asp Ile Asn Phe Ile Gly Pro Arg His Leu
        35                  40                  45

Ser Ala Thr Ala Ala Ser Leu Ser Gly Met Val Val Ala Val
    50                  55                  60

Leu Ala Gly Cys Val Val Gly Ser Leu Ile Ser Gly Trp Met Gly Ile
65                  70                  75                  80

Arg Phe Gly Arg Arg Gly Gly Leu Leu Ile Ser Ala Val Cys Phe Ile
                85                  90                  95

Ile Ser Gly Phe Gly Ala Ala Thr Thr Gly Leu Thr Gly Asp Ile Gly
            100                 105                 110

Ser Ala Leu Pro Ile Phe Cys Phe Phe Arg Phe Leu Gly Gly Phe Gly
        115                 120                 125

Ile Gly Ile Val Ser Thr Leu Thr Pro Thr Tyr Ile Ala Glu Ile Ala
    130                 135                 140
```

```
Pro Pro Asp Lys Arg Gly Gln Met Val Ser Gln Gln Met Ala Ile
145                 150                 155                 160

Val Thr Gly Ala Leu Thr Gly Tyr Ile Phe Thr Trp Leu Leu Ala His
            165                 170                 175

Phe Gly Ser Val Asp Trp Ile Asn Ala Asn Gly Trp Arg Trp Ser Pro
        180                 185                 190

Ala Ser Glu Gly Ile Ile Ala Val Phe Leu Leu Leu Leu Leu Thr
    195                 200                 205

Ala Pro Asp Thr Pro His Trp Leu Val Met Lys Gly Arg His Ser Glu
210                 215                 220

Ala Ser Lys Ile Leu Ala Arg Leu Glu Pro Gln Val Asp Pro Ser Leu
225                 230                 235                 240

Thr Ile Gln Lys Ile Lys Ala Gly Phe Asp Lys Ala Leu Gln Lys Ser
                245                 250                 255

Asn Ser Gly Leu Phe Ala Phe Gly Ala Thr Val Ile Phe Ala Gly Val
            260                 265                 270

Ser Val Ala Met Phe Gln Gln Leu Val Gly Ile Asn Ala Val Leu Tyr
        275                 280                 285

Tyr Ala Pro Gln Met Phe Leu Asn Leu Gly Phe Gly Ala Asp Thr Ala
    290                 295                 300

Leu Leu Gln Thr Ile Ser Ile Gly Val Val Asn Phe Val Phe Thr Met
305                 310                 315                 320

Ile Ala Ser Arg Ile Val Asp Arg Phe Gly Arg Lys Pro Leu Leu Ile
                325                 330                 335

Trp Gly Gly Ile Ala Met Ala Val Met Met Phe Ser Leu Gly Met Met
            340                 345                 350

Phe Thr Tyr His Ile Gly Gly Val Leu Pro Leu Ala Ala Ile Leu Leu
        355                 360                 365

Tyr Ile Val Gly Phe Ala Met Ser Trp Gly Pro Val Cys Trp Val Val
    370                 375                 380

Leu Ser Glu Met Phe Pro Asn Ala Ile Lys Gly Ser Ala Met Pro Ile
385                 390                 395                 400

Ala Val Thr Ala Gln Trp Ile Ala Asn Ile Leu Val Asn Phe Leu Phe
                405                 410                 415

Lys Ile Ala Asp Gly Asp Pro Gly Leu Asn Arg Thr Phe Asn His Gly
            420                 425                 430

Phe Ser Tyr Leu Val Phe Ala Gly Leu Ser Ile Leu Gly Ala Leu Ile
        435                 440                 445

Val Ala Arg Phe Val Pro Glu Thr Lys Gly Arg Ser Leu Glu Glu Ile
    450                 455                 460

Glu Glu Met Trp Arg Ser
465                 470

<210> SEQ ID NO 3
<211> LENGTH: 473
<212> TYPE: PRT
<213> ORGANISM: Zymomonas mobilis

<400> SEQUENCE: 3

Met Ser Ser Glu Ser Ser Gln Gly Leu Val Thr Arg Leu Ala Leu Ile
1               5                   10                  15

Ala Ala Ile Gly Gly Leu Leu Phe Gly Tyr Asp Ser Ala Val Ile Ala
            20                  25                  30

Ala Ile Gly Thr Pro Val Asp Ile His Phe Ile Ala Pro Arg His Leu
        35                  40                  45
```

-continued

```
Ser Ala Thr Ala Ala Ser Leu Ser Gly Met Val Val Ala Val
     50                  55                  60

Leu Val Gly Cys Val Thr Gly Ser Leu Leu Ser Gly Trp Ile Gly Ile
65                  70                  75                  80

Arg Phe Gly Arg Arg Gly Leu Leu Met Ser Ser Ile Cys Phe Val
                85                  90                  95

Ala Ala Gly Phe Gly Ala Ala Leu Thr Glu Lys Leu Phe Gly Thr Gly
                100                 105                 110

Gly Ser Ala Leu Gln Ile Phe Cys Phe Phe Arg Phe Leu Ala Gly Leu
            115                 120                 125

Gly Ile Gly Val Val Ser Thr Leu Thr Pro Thr Tyr Ile Ala Glu Ile
    130                 135                 140

Ala Pro Pro Asp Lys Arg Gly Gln Met Val Ser Gly Gln Gln Met Ala
145                 150                 155                 160

Ile Val Thr Gly Ala Leu Thr Gly Tyr Ile Phe Thr Trp Leu Leu Ala
                165                 170                 175

His Phe Gly Ser Ile Asp Trp Val Asn Ala Ser Gly Trp Cys Trp Ser
                180                 185                 190

Pro Ala Ser Glu Gly Leu Ile Gly Ile Ala Phe Leu Leu Leu Leu
            195                 200                 205

Thr Ala Pro Asp Thr Pro His Trp Leu Val Met Lys Gly Arg His Ser
    210                 215                 220

Glu Ala Ser Lys Ile Leu Ala Arg Leu Glu Pro Gln Ala Asp Pro Asn
225                 230                 235                 240

Leu Thr Ile Gln Lys Ile Lys Ala Gly Phe Asp Lys Ala Met Asp Lys
                245                 250                 255

Ser Ser Ala Gly Leu Phe Ala Phe Gly Ile Thr Val Val Phe Ala Gly
                260                 265                 270

Val Ser Val Ala Ala Phe Gln Gln Leu Val Gly Ile Asn Ala Val Leu
    275                 280                 285

Tyr Tyr Ala Pro Gln Met Phe Gln Asn Leu Gly Phe Gly Ala Asp Thr
    290                 295                 300

Ala Leu Leu Gln Thr Ile Ser Ile Gly Val Val Asn Phe Ile Phe Thr
305                 310                 315                 320

Met Ile Ala Ser Arg Val Val Asp Arg Phe Gly Arg Lys Pro Leu Leu
                325                 330                 335

Ile Trp Gly Ala Leu Gly Met Ala Ala Met Met Ala Val Leu Gly Cys
            340                 345                 350

Cys Phe Trp Phe Lys Val Gly Val Leu Pro Leu Ala Ser Val Leu
    355                 360                 365

Leu Tyr Ile Ala Val Phe Gly Met Ser Trp Gly Pro Val Cys Trp Val
    370                 375                 380

Val Leu Ser Glu Met Phe Pro Ser Ser Ile Lys Gly Ala Ala Met Pro
385                 390                 395                 400

Ile Ala Val Thr Gly Gln Trp Leu Ala Asn Ile Leu Val Asn Phe Leu
                405                 410                 415

Phe Lys Val Ala Asp Gly Ser Pro Ala Leu Asn Gln Thr Phe Asn His
            420                 425                 430

Gly Phe Ser Tyr Leu Val Phe Ala Ala Leu Ser Ile Leu Gly Gly Leu
            435                 440                 445

Ile Val Ala Arg Phe Val Pro Glu Thr Lys Gly Arg Ser Leu Asp Glu
    450                 455                 460
```

Ile Glu Glu Met Trp Arg Ser Gln Lys
465                 470

<210> SEQ ID NO 4
<211> LENGTH: 1476
<212> TYPE: DNA
<213> ORGANISM: Escherichia coli

<400> SEQUENCE: 4

```
atgaataccc agtataattc cagttatata ttttcgatta ccttagtcgc tacattaggt      60
ggtttattat ttggctacga caccgccgtt atttccggta ctgttgagtc actcaatacc     120
gtctttgttg ctccacaaaa cttaagtgaa tccgctgcca actccctgtt agggttttgc     180
gtggccagcg ctctgattgg ttgcatcatc ggcggtgccc tcggtggtta ttgcagtaac     240
cgcttcggtc gtcgtgattc acttaagatt gctgctgtcc tgttttttat ttctggtgta     300
ggttctgcct ggccagaact tggttttacc tctataaacc cggacaacac tgtgcctgtt     360
tatctggcag ttatgtcccg gaatttgtt atttatcgca ttattggcgg tattggcgtt     420
ggtttagcct caatgctctc gccaatgtat attgcggaac tggctccagc tcatattcgc     480
gggaaactgg tctcttttaa ccagtttgcg attattttcg gcaacttttt agtttactgc     540
gtaaactatt ttattgcccg ttccggtgat gccagctggc tgaatactga cggctggcgt     600
tatatgtttg cctcggaatg tatccctgca ctgctgttct aatgctgct gtataccgtg     660
ccagaaagtc ctcgctggct gatgtcgcgc ggcaagcaag aacaggcgga aggtatcctg     720
cgcaaaatta tggcaacac gcttgcaact caggcagtac aggaaattaa acactccctg     780
gatcatggcc gcaaaaccgg tggtcgtctg ctgatgtttg gcgtgggcgt gattgtaatc     840
ggcgtaatgc tctccatctt ccagcaattt gtcggcatca atgtggtgct gtactacgcg     900
ccggaagtgt tcaaaacgct gggggccagc acggatatcg cgctgttgca gaccattatt     960
gtcggagtta tcaacctcac cttcaccgtt ctggcaatta tgacggtgga taaatttggt    1020
cgtaagccac tgcaaattat cggcgcactc ggaatggcaa tcggtatgtt tagcctcggt    1080
accgcgtttt acactcaggc accgggtatt gtggcgctac tgtcgatgct gttctatgtt    1140
gccgcctttg ccatgtcctg gggtccggta tgctgggtac tgctgtcgga atcttcccg    1200
aatgctattc gtggtaaagc gctggcaatc gcggtggcgg cccagtggct ggcgaactac    1260
ttcgtctcct ggaccttccc gatgatggac aaaaactcct ggctggtggc ccatttccac    1320
aacggtttct cctactggat ttacggttgt atgggcgttc tggcagcact gtttatgtgg    1380
aaatttgtcc cggaaaccaa aggtaaaacc cttgaggagc tggaagcgct ctgggaaccg    1440
gaaacgaaga aaacacaaca aactgctacg ctgtaa                              1476
```

<210> SEQ ID NO 5
<211> LENGTH: 491
<212> TYPE: PRT
<213> ORGANISM: Escherichia coli

<400> SEQUENCE: 5

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
                20                  25                  30

Gly Thr Val Glu Ser Leu Asn Thr Val Phe Val Ala Pro Gln Asn Leu
            35                  40                  45

Ser Glu Ser Ala Ala Asn Ser Leu Leu Gly Phe Cys Val Ala Ser Ala

```
                 50                  55                  60
Leu Ile Gly Cys Ile Ile Gly Ala Leu Gly Gly Tyr Cys Ser Asn
 65                  70                  75                  80

Arg Phe Gly Arg Arg Asp Ser Leu Lys Ile Ala Ala Val Leu Phe Phe
                 85                  90                  95

Ile Ser Gly Val Gly Ser Ala Trp Pro Glu Leu Gly Phe Thr Ser Ile
                100                 105                 110

Asn Pro Asp Asn Thr Val Pro Val Tyr Leu Ala Gly Tyr Val Pro Glu
                115                 120                 125

Phe Val Ile Tyr Arg Ile Ile Gly Ile Gly Val Gly Leu Ala Ser
                130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Ser
                180                 185                 190

Trp Leu Asn Thr Asp Gly Trp Arg Tyr Met Phe Ala Ser Glu Cys Ile
                195                 200                 205

Pro Ala Leu Leu Phe Leu Met Leu Leu Tyr Thr Val Pro Glu Ser Pro
                210                 215                 220

Arg Trp Leu Met Ser Arg Gly Lys Gln Glu Gln Ala Glu Gly Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Gly Arg Leu Leu Met
                260                 265                 270

Phe Gly Val Gly Val Ile Val Gly Val Met Leu Ser Ile Phe Gln
                275                 280                 285

Gln Phe Val Gly Ile Asn Val Val Leu Tyr Tyr Ala Pro Glu Val Phe
                290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
                325                 330                 335

Asp Lys Phe Gly Arg Lys Pro Leu Gln Ile Ile Gly Ala Leu Gly Met
                340                 345                 350

Ala Ile Gly Met Phe Ser Leu Gly Thr Ala Phe Tyr Thr Gln Ala Pro
                355                 360                 365

Gly Ile Val Ala Leu Leu Ser Met Leu Phe Tyr Val Ala Ala Phe Ala
                370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
                420                 425                 430

Ser Trp Leu Val Ala His Phe His Asn Gly Phe Ser Tyr Trp Ile Tyr
                435                 440                 445

Gly Cys Met Gly Val Leu Ala Ala Leu Phe Met Trp Lys Phe Val Pro
                450                 455                 460

Glu Thr Lys Gly Lys Thr Leu Glu Glu Leu Glu Ala Leu Trp Glu Pro
465                 470                 475                 480
```

Glu Thr Lys Lys Thr Gln Gln Thr Ala Thr Leu
            485                 490

<210> SEQ ID NO 6
<211> LENGTH: 1323
<212> TYPE: DNA
<213> ORGANISM: Escherichia coli

<400> SEQUENCE: 6

```
atgcaagcct attttgacca gctcgatcgc gttcgttatg aaggctcaaa atcctcaaac      60
ccgttagcat tccgtcacta caatcccgac gaactggtgt tgggtaagcg tatggaagag     120
cacttgcgtt ttgccgcctg ctactggcac accttctgct ggaacggggc ggatatgttt     180
ggtgtggggg cgtttaatcg tccgtggcag cagcctggtg aggcactggc gttggcgaag     240
cgtaaagcag atgtcgcatt tgagttttt  cacaagttac atgtgccatt ttattgcttc     300
cacgatgtgg atgtttcccc tgagggcgcg tcgttaaaag agtacatcaa taattttgcg     360
caaatggttg atgtcctggc aggcaagcaa gaagagagcg gcgtgaagct gctgtgggga     420
acggccaact gctttacaaa ccctcgctac ggcgcgggtg cggcgacgaa cccagatcct     480
gaagtcttca gctgggcggc aacgcaagtt gttacagcga tggaagcaac ccataaattg     540
ggcggtgaaa actatgtcct gtgggcggt  cgtgaaggtt acgaaacgct gttaaatacc     600
gacttgcgtc aggagcgtga caactgggc  cgctttatgc agatggtggt tgagcataaa     660
cataaaatcg gtttccaggg cacgttgctt atcgaaccga accgcaagda accgaccaaa     720
catcaatatg attacgatgc cgcgacggtc tatggcttcc tgaaacagtt tggtctggaa     780
aaagagatta aactgaacat tgaagctaac cacgcgacgc tggcaggtca ctctttccat     840
catgaaatag ccaccgccat tgcgcttggc ctgttcggtt ctgtcgacgc caaccgtggc     900
gatgcgcaac tgggctggga caccgaccag ttcccgaaca gtgtggaaga gaatgcgctg     960
gtgatgtatg aaattctcaa gcaggcggtt tcaccaccg  tggtctgaa  cttcgatgcc    1020
aaagtacgtc gtcaaagtac tgataaatat gatctgtttt acggtcatat cggcgcgatg    1080
gatacgatgg cactggcgct gaaaattgca gcgcgcatga ttgaagatgg cgagctggat    1140
aaacgcatcg cgcagcgtta ttccggctgg aatagcgaat gggccagca  aatcctgaaa    1200
ggccaaatgt cactggcaga tttagccaaa tatgctcagg aacatcattt tgtctccggtg    1260
catcagagtg gtcgccagga caactggaa  atctggtaa  accattatct gttcgacaaa    1320
taa                                                                   1323
```

<210> SEQ ID NO 7
<211> LENGTH: 440
<212> TYPE: PRT
<213> ORGANISM: Escherichia coli

<400> SEQUENCE: 7

Met Gln Ala Tyr Phe Asp Gln Leu Asp Arg Val Arg Tyr Glu Gly Ser
1               5                   10                  15

Lys Ser Ser Asn Pro Leu Ala Phe Arg His Tyr Asn Pro Asp Glu Leu
            20                  25                  30

Val Leu Gly Lys Arg Met Glu His Leu Arg Phe Ala Ala Cys Tyr
        35                  40                  45

Trp His Thr Phe Cys Trp Asn Gly Ala Asp Met Phe Gly Val Gly Ala
    50                  55                  60

Phe Asn Arg Pro Trp Gln Gln Pro Gly Glu Ala Leu Ala Leu Ala Lys

```
                65                  70                  75                  80
Arg Lys Ala Asp Val Ala Phe Glu Phe Phe His Lys Leu His Val Pro
                        85                  90                  95

Phe Tyr Cys Phe His Asp Val Asp Val Ser Pro Glu Gly Ala Ser Leu
            100                 105                 110

Lys Glu Tyr Ile Asn Asn Phe Ala Gln Met Val Asp Val Leu Ala Gly
        115                 120                 125

Lys Gln Glu Glu Ser Gly Val Lys Leu Leu Trp Gly Thr Ala Asn Cys
    130                 135                 140

Phe Thr Asn Pro Arg Tyr Gly Ala Gly Ala Ala Thr Asn Pro Asp Pro
145                 150                 155                 160

Glu Val Phe Ser Trp Ala Ala Thr Gln Val Val Thr Ala Met Glu Ala
                165                 170                 175

Thr His Lys Leu Gly Gly Glu Asn Tyr Val Leu Trp Gly Gly Arg Glu
            180                 185                 190

Gly Tyr Glu Thr Leu Leu Asn Thr Asp Leu Arg Gln Glu Arg Glu Gln
        195                 200                 205

Leu Gly Arg Phe Met Gln Met Val Val Glu His Lys His Lys Ile Gly
    210                 215                 220

Phe Gln Gly Thr Leu Leu Ile Glu Pro Lys Pro Gln Glu Pro Thr Lys
225                 230                 235                 240

His Gln Tyr Asp Tyr Asp Ala Ala Thr Val Tyr Gly Phe Leu Lys Gln
                245                 250                 255

Phe Gly Leu Glu Lys Glu Ile Lys Leu Asn Ile Glu Ala Asn His Ala
            260                 265                 270

Thr Leu Ala Gly His Ser Phe His His Glu Ile Ala Thr Ala Ile Ala
        275                 280                 285

Leu Gly Leu Phe Gly Ser Val Asp Ala Asn Arg Gly Asp Ala Gln Leu
    290                 295                 300

Gly Trp Asp Thr Asp Gln Phe Pro Asn Ser Val Glu Glu Asn Ala Leu
305                 310                 315                 320

Val Met Tyr Glu Ile Leu Lys Ala Gly Gly Phe Thr Thr Gly Gly Leu
                325                 330                 335

Asn Phe Asp Ala Lys Val Arg Arg Gln Ser Thr Asp Lys Tyr Asp Leu
            340                 345                 350

Phe Tyr Gly His Ile Gly Ala Met Asp Thr Met Ala Leu Ala Leu Lys
        355                 360                 365

Ile Ala Ala Arg Met Ile Glu Asp Gly Glu Leu Asp Lys Arg Ile Ala
    370                 375                 380

Gln Arg Tyr Ser Gly Trp Asn Ser Glu Leu Gly Gln Gln Ile Leu Lys
385                 390                 395                 400

Gly Gln Met Ser Leu Ala Asp Leu Ala Lys Tyr Ala Gln Glu His His
                405                 410                 415

Leu Ser Pro Val His Gln Ser Gly Arg Gln Glu Gln Leu Glu Asn Leu
            420                 425                 430

Val Asn His Tyr Leu Phe Asp Lys
        435                 440

<210> SEQ ID NO 8
<211> LENGTH: 1455
<212> TYPE: DNA
<213> ORGANISM: Escherichia coli

<400> SEQUENCE: 8
```

```
atgtatatcg gatagatct tggcacctcg gcgtaaaag ttattttgct caacgagcag    60
ggtgaggtgg ttgctgcgca acggaaaag ctgaccgttt cgcgcccgca tccactctgg   120
tcggaacaag acccggaaca gtggtggcag gcaactgatc gcgcaatgaa agctctgggc  180
gatcagcatt ctctgcagga cgttaaagca ttgggtattg ccggccagat gcacggagca  240
accttgctgg atgctcagca acgggtgtta cgccctgcca ttttgtggaa cgacgggcgc  300
tgtgcgcaag agtgcacttt gctggaagcg cgagttccgc aatcgcgggt gattaccggc  360
aacctgatga tgcccggatt tactgcgcct aaattgctat gggttcagcg gcatgagccg  420
gagatattcc gtcaaatcga caaagtatta ttaccgaaag attacttgcg tctgcgtatg  480
acgggggagt ttgccagcga tatgtctgac gcagctggca ccatgtggct ggatgtcgca  540
aagcgtgact ggagtgacgt catgctgcag gcttgcgact tatctcgtga ccagatgccc  600
gcattatacg aaggcagcga aattactggt gctttgttac ctgaagttgc gaaagcgtgg  660
ggtatggcga cggtgccagt tgtcgcaggc ggtggcgaca atgcagctgg tgcagttggt  720
gtgggaatgg ttgatgctaa tcaggcaatg ttatcgctgg ggacgtcggg ggtctatttt  780
gctgtcagcg aagggttctt aagcaagcca gaaagcgccg tacatagctt tgccatgcg   840
ctaccgcaac gttggcattt aatgtctgtg atgctgagtg cagcgtcgtg tctggattgg  900
gccgcgaaat taaccggcct gagcaatgtc ccagctttaa tcgctgcagc tcaacaggct  960
gatgaaagtg ccgagccagt ttggtttctg ccttatcttt ccggcgagcg tacgccacac 1020
aataatcccc aggcgaaggg ggttttcttt ggtttgactc atcaacatgg ccccaatgaa 1080
ctggcgcgag cagtgctgga aggcgtgggt tatgcgctgg cagatggcat ggatgtcgtg 1140
catgcctgcg gtattaaacc gcaaagtgtt acgttgattg ggggcggggc gcgtagtgag 1200
tactggcgtc agatgctggc ggatatcagc ggtcagcagc tcgattaccg tacgggggg  1260
gatgtggggc cagcactggg cgcagcaagg ctggcgcaga tcgcggcgaa tccagagaaa 1320
tcgctcattg aattgttgcc gcaactaccg ttagaacagt cgcatctacc agatgcgcag 1380
cgttatgccg cttatcagcc acgacgagaa acgttccgtc gcctctatca gcaacttctg 1440
ccattaatgg cgtaa                                                 1455
```

<210> SEQ ID NO 9
<211> LENGTH: 484
<212> TYPE: PRT
<213> ORGANISM: Escherichia coli

<400> SEQUENCE: 9

```
Met Tyr Ile Gly Ile Asp Leu Gly Thr Ser Gly Val Lys Val Ile Leu
1               5                   10                  15

Leu Asn Glu Gln Gly Glu Val Ala Ala Gln Thr Glu Lys Leu Thr
            20                  25                  30

Val Ser Arg Pro His Pro Leu Trp Ser Glu Gln Asp Pro Glu Gln Trp
        35                  40                  45

Trp Gln Ala Thr Asp Arg Ala Met Lys Ala Leu Gly Asp Gln His Ser
    50                  55                  60

Leu Gln Asp Val Lys Ala Leu Gly Ile Ala Gly Gln Met His Gly Ala
65                  70                  75                  80

Thr Leu Leu Asp Ala Gln Gln Arg Val Leu Arg Pro Ala Ile Leu Trp
                85                  90                  95

Asn Asp Gly Arg Cys Ala Gln Glu Cys Thr Leu Leu Glu Ala Arg Val
            100                 105                 110
```

Pro Gln Ser Arg Val Ile Thr Gly Asn Leu Met Met Pro Gly Phe Thr
            115                 120                 125

Ala Pro Lys Leu Leu Trp Val Gln Arg His Glu Pro Glu Ile Phe Arg
130                 135                 140

Gln Ile Asp Lys Val Leu Leu Pro Lys Asp Tyr Leu Arg Leu Arg Met
145                 150                 155                 160

Thr Gly Glu Phe Ala Ser Asp Met Ser Asp Ala Ala Gly Thr Met Trp
                165                 170                 175

Leu Asp Val Ala Lys Arg Asp Trp Ser Asp Val Met Leu Gln Ala Cys
            180                 185                 190

Asp Leu Ser Arg Asp Gln Met Pro Ala Leu Tyr Glu Gly Ser Glu Ile
        195                 200                 205

Thr Gly Ala Leu Leu Pro Glu Val Ala Lys Ala Trp Gly Met Ala Thr
210                 215                 220

Val Pro Val Val Ala Gly Gly Asp Asn Ala Ala Gly Ala Val Gly
225                 230                 235                 240

Val Gly Met Val Asp Ala Asn Gln Ala Met Leu Ser Leu Gly Thr Ser
                245                 250                 255

Gly Val Tyr Phe Ala Val Ser Glu Gly Phe Leu Ser Lys Pro Glu Ser
            260                 265                 270

Ala Val His Ser Phe Cys His Ala Leu Pro Gln Arg Trp His Leu Met
        275                 280                 285

Ser Val Met Leu Ser Ala Ala Ser Cys Leu Asp Trp Ala Ala Lys Leu
290                 295                 300

Thr Gly Leu Ser Asn Val Pro Ala Leu Ile Ala Ala Gln Gln Ala
305                 310                 315                 320

Asp Glu Ser Ala Glu Pro Val Trp Phe Leu Pro Tyr Leu Ser Gly Glu
                325                 330                 335

Arg Thr Pro His Asn Asn Pro Gln Ala Lys Gly Val Phe Phe Gly Leu
            340                 345                 350

Thr His Gln His Gly Pro Asn Glu Leu Ala Arg Ala Val Leu Glu Gly
        355                 360                 365

Val Gly Tyr Ala Leu Ala Asp Gly Met Asp Val Val His Ala Cys Gly
370                 375                 380

Ile Lys Pro Gln Ser Val Thr Leu Ile Gly Gly Gly Ala Arg Ser Glu
385                 390                 395                 400

Tyr Trp Arg Gln Met Leu Ala Asp Ile Ser Gly Gln Gln Leu Asp Tyr
                405                 410                 415

Arg Thr Gly Gly Asp Val Gly Pro Ala Leu Gly Ala Ala Arg Leu Ala
            420                 425                 430

Gln Ile Ala Ala Asn Pro Glu Lys Ser Leu Ile Glu Leu Leu Pro Gln
        435                 440                 445

Leu Pro Leu Glu Gln Ser His Leu Pro Asp Ala Gln Arg Tyr Ala Ala
450                 455                 460

Tyr Gln Pro Arg Arg Glu Thr Phe Arg Arg Leu Tyr Gln Gln Leu Leu
465                 470                 475                 480

Pro Leu Met Ala

<210> SEQ ID NO 10
<211> LENGTH: 966
<212> TYPE: DNA
<213> ORGANISM: Escherichia coli

<400> SEQUENCE: 10

-continued

```
atgacaaagt atgcattagt cggtgatgtg gcggcacca acgcacgtct tgctctgtgt      60
gatattgcca gtggtgaaat ctcgcaggct aagacctatt cagggcttga ttaccccagc    120
ctcgaagcgg tcattcgcgt ttatcttgaa gaacataagg tcgaggtgaa agacggctgt    180
attgccatcg cttgcccaat taccggtgac tgggtggcga tgaccaacca tacctgggcg    240
ttctcaattg ccgaaatgaa aaagaatctc ggttttagcc atctggaaat tattaacgat    300
tttaccgctg tatcgatggc gatcccgatg ctgaaaaaag agcatctgat tcagtttggt    360
ggcgcagaac cggtcgaagg taagcctatt gcggtttacg gtgccggaac ggggcttggg    420
gttgcgcatc tggtccatgt cgataagcgt tgggtaagct tgccaggcga aggcggtcac    480
gttgattttg cgccgaatag tgaagaagag gccattatcc tcgaaatatt gcgtgcggaa    540
attggtcatg tttcggcgga gcgcgtgctt tctggccctg gctggtgaa tttgtatcgc     600
gcaattgtga agctgacaa ccgcctgcca gaaaatctca gccaaaaga tattaccgaa      660
cgcgcgctgg ctgacagctg caccgattgc cgccgcgcat tgtcgctgtt ttgcgtcatt    720
atgggccgtt ttggcggcaa tctggcgctc aatctcggga catttggcgg cgtgtttatt    780
gcgggcggta tcgtgccgcg cttccttgag ttcttcaaag cctccggttt ccgtgccgca    840
tttgaagata aagggcgctt taagaatat gtccatgata ttccggtgta tctcatcgtc     900
catgacaatc cgggccttct cggttccggt gcacatttac gccagacctt aggtcacatt    960
ctgtaa                                                               966
```

<210> SEQ ID NO 11
<211> LENGTH: 321
<212> TYPE: PRT
<213> ORGANISM: Escherichia coli

<400> SEQUENCE: 11

```
Met Thr Lys Tyr Ala Leu Val Gly Asp Val Gly Gly Thr Asn Ala Arg
1               5                   10                  15

Leu Ala Leu Cys Asp Ile Ala Ser Gly Glu Ile Ser Gln Ala Lys Thr
            20                  25                  30

Tyr Ser Gly Leu Asp Tyr Pro Ser Leu Glu Ala Val Ile Arg Val Tyr
        35                  40                  45

Leu Glu Glu His Lys Val Glu Val Lys Asp Gly Cys Ile Ala Ile Ala
    50                  55                  60

Cys Pro Ile Thr Gly Asp Trp Val Ala Met Thr Asn His Thr Trp Ala
65                  70                  75                  80

Phe Ser Ile Ala Glu Met Lys Lys Asn Leu Gly Phe Ser His Leu Glu
                85                  90                  95

Ile Ile Asn Asp Phe Thr Ala Val Ser Met Ala Ile Pro Met Leu Lys
            100                 105                 110

Lys Glu His Leu Ile Gln Phe Gly Gly Ala Glu Pro Val Glu Gly Lys
        115                 120                 125

Pro Ile Ala Val Tyr Gly Ala Gly Thr Gly Leu Gly Val Ala His Leu
    130                 135                 140

Val His Val Asp Lys Arg Trp Val Ser Leu Pro Gly Glu Gly Gly His
145                 150                 155                 160

Val Asp Phe Ala Pro Asn Ser Glu Glu Glu Ala Ile Ile Leu Glu Ile
                165                 170                 175

Leu Arg Ala Glu Ile Gly His Val Ser Ala Glu Arg Val Leu Ser Gly
            180                 185                 190

Pro Gly Leu Val Asn Leu Tyr Arg Ala Ile Val Lys Ala Asp Asn Arg
```

195                 200                 205

Leu Pro Glu Asn Leu Lys Pro Lys Asp Ile Thr Glu Arg Ala Leu Ala
    210                 215                 220

Asp Ser Cys Thr Asp Cys Arg Arg Ala Leu Ser Leu Phe Cys Val Ile
225                 230                 235                 240

Met Gly Arg Phe Gly Gly Asn Leu Ala Leu Asn Leu Gly Thr Phe Gly
                245                 250                 255

Gly Val Phe Ile Ala Gly Gly Ile Val Pro Arg Phe Leu Glu Phe Phe
            260                 265                 270

Lys Ala Ser Gly Phe Arg Ala Ala Phe Glu Asp Lys Gly Arg Phe Lys
        275                 280                 285

Glu Tyr Val His Asp Ile Pro Val Tyr Leu Ile Val His Asp Asn Pro
    290                 295                 300

Gly Leu Leu Gly Ser Gly Ala His Leu Arg Gln Thr Leu Gly His Ile
305                 310                 315                 320

Leu

<210> SEQ ID NO 12
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 12 cctttttacgg ctagctcagc cctaggtatt atgctagcgc t                 41

<210> SEQ ID NO 13
<211> LENGTH: 45
<212> TYPE: DNA
<213> ORGANISM: Artificial Sequence
<220> FEATURE:
<223> OTHER INFORMATION: Synthetic polynucleotide

<400> SEQUENCE: 13
ctagagcgct agcataatac ctagggctga gctagccgta aaagg             45

<210> SEQ ID NO 14
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 14
aaaacatatg cctgacgcta aaaaacagg                                29

<210> SEQ ID NO 15
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 15
aaaaaagctt gtttaaactt ttctcgagtt ttgtcgactt aatcgtgagc gcctatttcg   60

<210> SEQ ID NO 16
<211> LENGTH: 49
<212> TYPE: DNA
<213> ORGANISM: Artificial Sequence
<220> FEATURE:

<223> OTHER INFORMATION: Synthetic polynucleotide

<400> SEQUENCE: 16
aaaagtcgac aaggaggaat aaaccatgac aaagtatgca ttagtcggt            49

<210> SEQ ID NO 17
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 17
aaaagtttaa acttacagaa tgtgacctaa ggtctg                          36

<210> SEQ ID NO 18
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 18
aaaacatatg agttcagaaa gtagtcaagg tct                             33

<210> SEQ ID NO 19
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 19
aaaagtcgac ttaggagcgc cacatctcc                                  29

<210> SEQ ID NO 20
<211> LENGTH: 64
<212> TYPE: DNA
<213> ORGANISM: Artificial Sequence
<220> FEATURE:
<223> OTHER INFORMATION: Synthetic polynucleotide

<400> SEQUENCE: 20
ggcaaggtgt tctggtcggc gcatagctga gataaatgct tcaataatat tgaaaagga  60 agag                                                             64

<210> SEQ ID NO 21
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 21
aggcaaagaa aacccggcgc tgaggccggg ttaccaatgc ttaatcagtg aggcaccta  59

<210> SEQ ID NO 22
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 22
ccacaacact aaacctataa gttggggaaa tacaatgttc attccgggga tccgtcgacc  60

```
<210> SEQ ID NO 23
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 23
taaccggggt tcacccacg gttacgctac cggacagttt tgtaggctgg agctgcttcg    60

<210> SEQ ID NO 24
<211> LENGTH: 140
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t

<400> SEQUENCE: 24
tctttcatac aatgacatat taaaatatca gcaagaattc caaagggtga aacaaaacgg    60
ttnacaacat gaagtaaaca cggtacgntg taccacatga aacgacagtg agtcaagcct   120
ggccataagg agatatacat                                               140

<210> SEQ ID NO 25
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 25
ttgaaatact tcgaattgat attcagacat ttctgcccat gtttgctgaa aggacaagtt    60
ttggtgactg                                                          70

<210> SEQ ID NO 26
<211> LENGTH: 42
<212> TYPE: DNA
<213> ORGANISM: Artificial Sequence
<220> FEATURE:
<223> OTHER INFORMATION: Synthetic polynucleotide

<400> SEQUENCE: 26
aaaacatatg aatacccagt ataattccag ttatatatttt tc                     42

<210> SEQ ID NO 27
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 27
aaaaaagctt gtttaaactt ttctcgagtt acagcgtagc agtttgttgt               50

<210> SEQ ID NO 28
<211> LENGTH: 132
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t

<400> SEQUENCE: 28
aagagaaaaa tgcaataagt acaattgcgc aacaaaagta agatcggttt ttttaggcct      60
ttnacagcta gctcagtcct aggtatnntg ctagcatact agaggccagc ctggccataa     120
ggagatatac at                                                         132

<210> SEQ ID NO 29
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 29
tcaagaacgg cgtttggttg cggagtccat ccatactgcc agcaactgaa aggacaagtt      60
ttggtgactg                                                             70

<210> SEQ ID NO 30
<211> LENGTH: 156
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 30
gaactccata atcaggtaat gccgcgggtg atggatgatg tcgtaannat aggcactccc      60
tttaaatatg tnaagaatta tttttataga acgcagctgc gggctgttac cgcgttcggg     120
tgcgataaaa agtaagatcg gttttttttag gcctttt                             156

<210> SEQ ID NO 31
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 31
tcaagaacgg cgtttggttg cggagtccat ccatactgcc agcaactgaa aggacaagtt      60
ttggtgactg                                                             70

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide
```

```
<400> SEQUENCE: 32
ccgattgtga cgcctgtaaa                                                      20

<210> SEQ ID NO 33
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 33
cgcaagtgct cttccatacg                                                      20

<210> SEQ ID NO 34
<211> LENGTH: 132
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t

<400> SEQUENCE: 34
aagagaaaaa tgcaataagt acaattgcgc aacaaaagta agatcggttt ttttaggcct          60
ttnacagcta gctcagtcct aggtatnntg ctagcatact agaggccagc ctggccataa        120
ggagatatac at                                                            132

<210> SEQ ID NO 35
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 35
tcaagaacgg cgtttggttg cggagtccat ccatactgcc agcaactgaa aggacaagtt         60
ttggtgactg                                                                70

<210> SEQ ID NO 36
<211> LENGTH: 156
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t

<400> SEQUENCE: 36
gaactccata atcaggtaat gccgcgggtg atggatgatg tcgtaannat aggcactccc         60
tttaaatatg tnaagaatta ttttatagaa acgcagctgc gggctgttac cgcgttcggg        120
tgcgataaaa agtaagatcg gttttttttag gccttt                                 156
```

```
<210> SEQ ID NO 37
<211> LENGTH: 70
<212> TYPE: DNA
<213> ORGANISM: Artificial Sequence
<220> FEATURE:
<223> OTHER INFORMATION: Synthetic polynucleotide

<400> SEQUENCE: 37
tcaagaacgg cgtttggttg cggagtccat ccatactgcc agcaactgaa aggacaagtt    60
ttggtgactg                                                           70
```